United States Patent [19]
Gelfand et al.

[11] Patent Number: 5,968,799
[45] Date of Patent: Oct. 19, 1999

[54] PURIFIED THERMOSTABLE NUCLEIC ACID POLYMERASE ENZYME FROM *THERMOSIPHO AFRICANUS*

[75] Inventors: David H. Gelfand, Oakland; I. Lawrence Greenfield, Pleasant Hill; Fred L. Reichert, Oakland, all of Calif.

[73] Assignee: Roche Molecular Systems, Inc., Pleasanton, Calif.

[21] Appl. No.: 07/977,428
[22] PCT Filed: Sep. 26, 1991
[86] PCT No.: PCT/US91/07076
  § 371 Date: Feb. 9, 1993
  § 102(e) Date: Feb. 9, 1993
[87] PCT Pub. No.: WO92/06202
  PCT Pub. Date: Apr. 16, 1992

Related U.S. Application Data

[63] Continuation-in-part of application No. 07/590,490, Sep. 28, 1990, abandoned.

[51] Int. Cl.⁶ ........................................ C12N 9/12
[52] U.S. Cl. ............................................. 435/194
[58] Field of Search ............................ 435/194; 935/10, 935/14

[56] References Cited

U.S. PATENT DOCUMENTS

| | | | |
|---|---|---|---|
| 4,889,818 | 12/1989 | Gelfand et al. | 435/194 |
| 4,965,188 | 10/1990 | Mullis et al. | 435/6 |
| 5,210,036 | 5/1993 | Comb et al. | 435/194 |

FOREIGN PATENT DOCUMENTS 8906691  7/1989  WIPO.

OTHER PUBLICATIONS

Simpson et al., 1990, "Purification and Some Properties of a Thermostable DNA Polymerase From a Thermotoga Species" Biochem. Cell Biol. 68:1292–1296.

Chein et al., 1976, "Deoxyribonucleic Acid Polymerase from the Extreme Thermophile Thermus aquaticus" J. Bacteriology 127(3):1550–1557.

Kaledin et al., 1980, "Isolation and Properties of DNA Polymerase From Extremely Thermophilic Bacterium Thermus aquaticus YT1" Biochem. 45(4):494–501.

Suggs et al., 1981, "Use of Synthetic Oligonucleotides as Hybridization Probes: Isolation of Cloned cDNA Sequences for Human Beta 2 Microglobulin" Proc. Natl. Acad. Sci. USA 78(11):6613–6617.

Young et al., 1983, "Efficient Isolation of Genes by Using Antibody Probes" Proc. Natl. Acad. Sci. USA 80:1194–1198.

Bernad et al., 1989, "A Conserved 3'–5' Exonuclease Active Site in Prokaryotic and Euckaryotic DNA Polymerases" Cell 59(a):219–228.

Huber et al., 1989, "*Thermosipho africanus* gen. nov., Represents a New Genus of Thermophilic Eubacteria Within the 'Thermotogales'" System. Appl. Microbiol. 12:32–37.

Lawyer et al., 1989, "Isolation, Characterization, and Expression in *Escherichia coli* of the DNA Polymerase Gene From Thermus aquaticus" J. Biological Chemistry 264:(11):6427–6437.

Leavitt et al., 1989, "T5 DNA Polymerase: Structural–Functional Relationships to Other DNA Polymerases" Proc. Natl. Acad. Sci. USA 86(12):4465–4469.

Gelfand, D.H. "Taq DNA Polymerase" PCR Technology, Principles and Applications for DNA Amplification Ed. Erlich, H.A. Stockton Press, pp. 17–22, 1992.

Derby Shire et al., *Science*, vol. 240, Apr. 8, 1988, pp. 199–201.

*Primary Examiner*—Keith D. Hendricks
*Attorney, Agent, or Firm*—Douglas A. Petry

[57] ABSTRACT

A purified thermostable enzyme is derived from the eubacterium *Thermosipho africanus*. The enzyme has DNA polymerase, activity reverse transcriptase activity, and optionally 5'→3' and/or 3'→5' exonuclease activity. The enzyme can be native or recombinant, and may be used with primers and nucleoside triphosphates in a temperature-cycling chain reaction where at least one nucleic acid sequence is amplified in quantity from an existing sequence.

2 Claims, 3 Drawing Sheets

PROFILE 1: ON CHROMOSOMAL DNA

PROFILE 2: ON PURIFIED ACRYLAMIDE FRAGMENT

PROFILE 3: ON LOWMELTING AGAROSE FRAGMENT
CHROMOSOMAL AMPLIFICATION IDENTICAL TO PROFILE 1

PROFILE 4: ON LOW MELTING AGAROSE FRAGMENT

PROFILE 5: ON LOW MELTING AGAROSE FRAGMENT
IDENTICAL TO CHROMOSOME $$\frac{OB-7}{DG154-DG155 + DG160-DG163}$$

PURIFIED THERMOSTABLE NUCLEIC ACID POLYMERASE ENZYME FROM *THERMOSIPHO AFRICANUS*

This application is a continuation-in-part of U.S. Ser. No. 07/590,490, filed Sep. 28, 1990, now abandoned.

FIELD OF THE INVENTION

The present invention relates to a purified, thermostable DNA polymerase purified from the thermophilic bacteria *Thermosipho africanus* (Taf) and means for isolating and producing the enzyme. Thermostable DNA polymerases are useful in many recombinant DNA techniques, especially nucleic acid amplification by the polymerase chain reaction (PCR).

BACKGROUND ART

Extensive research has been conducted on the isolation of DNA polymerases from mesophilic microorganisms such as *E. coli*. See, for example, Bessman et al., 1957, *J. Biol. Chem.* 223:171–177, and Buttin and Kornberg, 1966, *J. Biol. Chem.* 241:5419–5427.

Much less investigation has been made on the isolation and purification of DNA polymerases from thermophiles such as Taf. Kaledin et al., 1980, Biokhymiya 45:644–651, disclose a six-step isolation and purification procedure of DNA polymerase from cells of *Thermus aquaticus* YT-1 strain. These steps involve isolation of crude extract, DEAE-cellulose chromatography, fractionation on hydroxyapatite, fractionation on DEAE-cellulose, and chromatography on single-strand DNA-cellulose. The molecular weight of the purified enzyme is reported as 62,000 daltons per monomeric unit.

A second purification scheme for a polymerase from *Thermus aquaticus* is described by Chien et al., 1976, *J. Bacteriol.* 127:1550–1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons and by sucrose gradient centrifugation of about 68,000 daltons.

The use of thermostable enzymes, such as those described in U.S. Pat. No. 4,889,818, to amplify existing nucleic acid sequences in amounts that are large compared to the amount initially present was described U.S. Pat. Nos. 4,683,195 and 4,683,202, which describe the PCR process, both disclosures of which are incorporated herein by reference. Primers, template, nucleoside triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. The two patents disclose that, if the polymerase employed is a thermostable enzyme, then polymerase need not be added after every denaturation step, because heat will not destroy the polymerase activity.

U.S. Pat. No. 4,889,818, European Patent Publication No. 258,017, and PCT Publication No. 89/06691, the disclosures of which are incorporated herein by reference, all describe the isolation and recombinant expression of an ~94 kDa thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques such as DNA sequencing, nick-translation, and even reverse transcription. The present invention helps meet that need by providing recombinant expression vectors and purification protocols for a DNA polymerase from Taf.

SUMMARY OF THE INVENTION

Accordingly, the present invention provides a purified thermostable enzyme that catalyzes combination of nucleoside triphosphates to form a nucleic acid strand complementary to a nucleic acid template strand. The purified enzyme is the DNA polymerase activity from Taf. In a preferred embodiment, the enzyme is isolated from Taf strain OB-7 (DSM 5309). This purified material may be used in a temperature-cycling amplification reaction wherein nucleic acid sequences are produced from a given nucleic acid sequence in amounts that are large compared to the amount initially present so that the sequences can be manipulated and/or analyzed easily.

The gene encoding Taf DNA polymerase enzyme from Taf has also been identified and cloned and provides yet another means to prepare the thermostable enzyme of the present invention. In addition to the portions of the gene encoding the Taf enzyme, derivatives of these gene portions encoding Taf DNA polymerase activity are also provided.

The invention also encompasses a stable enzyme composition comprising a purified, thermostable Taf enzyme as described above in a buffer containing one or more non-ionic polymeric detergents.

Finally, the invention provides a method of purification for the thermostable polymerase of the invention. This method involves preparing a crude extract from Taf or recombinant host cells, adjusting the ionic strength of the crude extract so that the DNA polymerase dissociates from nucleic acid in the extract, subjecting the extract to at least one chromatographic step selected from hydrophobic interaction chromatography, DNA binding protein affinity chromatography, nucleotide binding protein affinity chromatography, and cation, anion, or hydroxyapatite chromatography. In a preferred embodiment, these steps are performed sequentially in the order given above. The nucleotide binding protein affinity chromatography step is preferred for separating the DNA polymerase from endonuclease proteins.

DETAILED DESCRIPTION OF THE INVENTION

Figure 1:
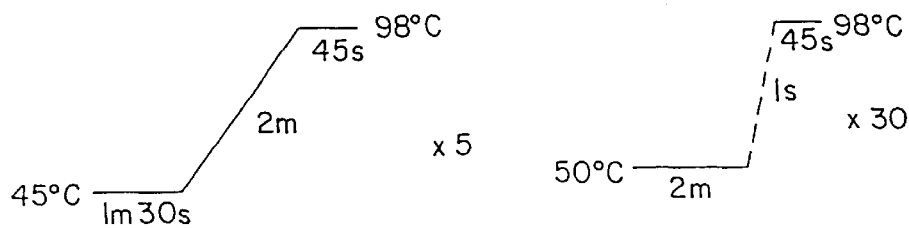
FIG. 1 shows various PCR profiles.
Figure 1:
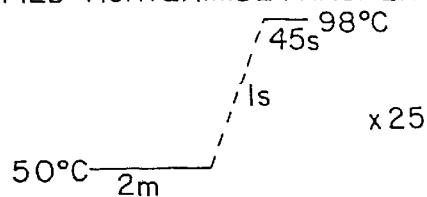
Figure 1:
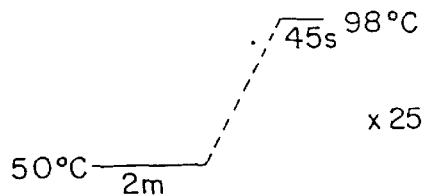
Figure 1:
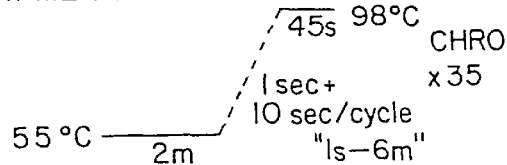
Figure 1:
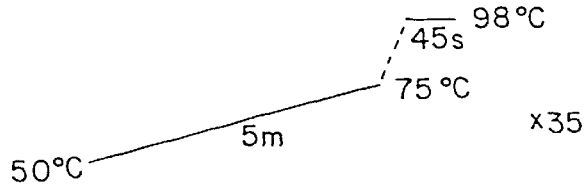

The present invention provides DNA sequences and expression vectors that encode Taf DNA polymerase. To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length gene sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing Taf polymerase refers to a collection of materials which includes Taf polymerase but which can also include other proteins. If the Taf polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized for purposes of this invention, by an ability to stabilize the Taf enzyme at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or be produced synthetically. Synthesis of a primer extension product which is complementary to a nucleic acid strand is initiated in the presence of four different nucleoside triphosphates and the Taf thermostable enzyme in an appropriate buffer at a suitable temperature. A "buffer" includes cofactors (such as divalent metal ions) and salt (to provide the appropriate ionic strength), adjusted to the desired pH. For Taf polymerase, the buffer preferably contains 1 to 3 mM of a magnesium salt, preferably $MgCl_2$, 50 to 200 $\mu$M of each nucleotide, and 0.2 to 1 $\mu$M of each primer, along with 50 mM KCl, 10 mM Tris buffer (pH 8.0–8.4), and 100 $\mu$g/ml gelatin (although gelatin is not required, and should be avoided in some applications, such as DNA sequencing).

A primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length and nucleotide sequence to ensure proper annealing of primer to template. Depending on the complexity of the target sequence, an oligonucleotide primer typically contains 15 to 35 nucleotides. Short primer molecules generally require lower temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The terms "thermostable polymerase" and "thermostable enzyme" refer to an enzyme which is stable to heat and is heat resistant and catalyzes (facilitates) combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

The Taf thermostable enzyme of the present invention satisfies the requirements for effective use in the amplification reaction known as the polymerase chain reaction or PCR. The Taf enzyme does not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° C. to about 105° C. for a time depending mainly on the temperature and the nucleic acid length, typically from a few seconds up to four minutes.

Higher temperatures may be required as the buffer salt concentration and/or GC composition of the nucleic acid is increased. The Taf enzyme does not become irreversibly denatured for relatively short exposures to temperatures of about 90° C.–100° C.

The Taf thermostable enzyme has an optimum temperature at which it functions that is higher than about 45° C. Temperatures below 45° C. facilitate hybridization of primer to template, but depending on salt composition and concentration and primer composition and length, hybridization of primer to template can occur at higher temperatures (e.g., 45–70° C.), which may promote specificity of the primer hybridization reaction. The Taf enzyme exhibits activity over a broad temperature range from about 37° C. to 90° C.

The present invention provides DNA sequences encoding the thermostable DNA polymerase activity of Taf. The encoded amino acid sequence has homology to portions of the thermostable DNA polymerases of Thermus species Z05 (TZ05), *Thermotoga maritima* (Tma), *Thermus aquaticus* (Taq) strain YT1, *T. thermophilus* (Tth), and Thermus species sps17 (Tsps17). The entire Taf coding sequence and the deduced amino acid sequence is depicted below as SEQ ID NO: 1. The amino acid sequences is also listed as SEQ ID NO: 2. For convenience, the amino acid sequence of this Taf polymerase is numbered for reference. Portions of the 5' and 3' noncoding regions of the Taf DNA polymerase gene are also shown.

```
   1 GAATTCTTGAAGAAGGGACTTTAAATACTAAGAGGTTTTTTAACT

46 TAGATGGAAATGTTTACAAAAAGGGTGCATTAGATGAGAAAACAA

91 AGGAATTAATGGGACTTGTTGCTTCAATGGTTTTAAGGTGTGATG

136 ATTGTATTACTTATCATATGATAAGGTGTGCACAACTTGGAGTTA

181 GTGATGAAGAATTTTTTGAAACTTTTGATGTGGCATTGATAGTTG

226 GAGGTTCAATAGTAATTCCTCATTTAAGACGTGCTGTTAAATTGC

271 TTGAGGATATCAGGGAGATGCAAAAAAATGGGAAAGATGTTTCTA
   1                                 MetGlyLysMetPheLeu

316 TTTGATGGAACTGGATTAGTATACAGAGCATTTTATGCTATAGAT
   7 PheAspGlyThrGlyLeuValTyrArgAlaPheTyrAlaIleAsp

361 CAATCTCTTCAAACTTCGTCTGGTTTACACACTAATGCTGTATAC
  22 GlnSerLeuGlnThrSerSerGlyLeuHisThrAsnAlaValTyr

406 GGACTTACTAAAATGCTTATAAAATTTTTAAAAGAACATATCAGT
  37 GlyLeuThrLysMetLeuIleLysPheLeuLysGluHisIleSer

451 ATTGGAAAAGATGCTTGTGTTTTTGTTTTAGATTCAAAAGGTGGT
  52 IleGlyLysAspAlaCysValPheValLeuAspSerLysGlyGly

496 AGCAAAAAAAGAAAGGATATTCTTGAAACATATAAAGCAAATAGG
  67 SerLysLysArgLysAspIleLeuGluThrTyrLysAlaAsnArg

541 CCATCAACGCCTGATTTACTTTTAGAGCAAATTCCATATGTAGAA
  82 ProSerThrProAspLeuLeuLeuGluGlnIleProTyrValGlu

586 GAACTTGTTGATGCTCTTGGAATAAAAGTTTTAAAAATAGAAGGC
  97 GluLeuValAspAlaLeuGlyIleLysValLeuLysIleGluGly

631 TTTGAAGCTGATGACATTATTGCTACGCTTTCTAAAAAATTTGAA
 112 PheGluAlaAspAspIleIleAlaThrLeuSerLysLysPheGlu

676 AGTGATTTTGAAAAGGTAAACATAATAACTGGAGATAAAGATCTT
 127 SerAspPheGluLysValAsnIleIleThrGlyAspLysAspLeu

721 TTACAACTTGTTTCTGATAAGGTTTTTGTTTGGAGAGTAGAAAGA
 142 LeuGlnLeuValSerAspLysValPheValTrpArgValGluArg

766 GGAATAACAGATTTGGTATTGTACGATAGAAATAAAGTGATTGAA
 157 GlyIleThrAspLeuValLeuTyrAspArgAsnLysValIleGlu

811 AAATATGGAATCTACCCAGAACAATTCAAAGATTATTTATCTCTT
 172 LysTyrGlyIleTyrProGluGlnPheLysAspTyrLeuSerLeu

856 GTCGGTGATCAGATTGATAATATCCCAGGAGTTAAAGGAATAGGA
 187 ValGlyAspGlnIleAspAsnIleProGlyValLysGlyIleGly

901 AAGAAAACAGCTGTTTCGCTTTTGAAAAAATATAATAGCTTGGAA
 202 LysLysThrAlaValSerLeuLeuLysLysTyrAsnSerLeuGlu

946 AATGTATTAAAAAATATTAACCTTTTGACGGAAAAATTAAGAAGG
 217 AsnValLeuLysAsnIleAsnLeuLeuThrGluLysLeuArgArg

991 CTTTTGGAAGATTCAAAGGAAGATTTGCAAAAAAGTATAGAACTT
 232 LeuLeuGluAspSerLysGluAspLeuGlnLysSerIleGluLeu

1036 GTGGAGTTGATATATGATGTACCAATGGATGTGGAAAAAGATGAA
 247 ValGluLeuIleTyrAspValProMetAspValGluLysAspGlu

1081 ATAATTTATAGAGGGTATAATCCAGATAAGCTTTTAAAGGTATTA
 262 IleIleTyrArgGlyTyrAsnProAspLysLeuLeuLysValLeu

1126 AAAAAGTACGAATTTTCATCTATAATTAAGGAGTTAAATTTACAA
 277 LysLysTyrGluPheSerSerIleIleLysGluLeuAsnLeuGln

1171 GAAAAATTAGAAAAGGAATATATACTGGTAGATAATGAAGATAAA
 292 GluLysLeuGluLysGluTyrIleLeuValAspAsnGluAspLys

1216 TTGAAAAAACTTGCAGAAGAGATAGAAAAATACAAAACTTTTTCA
 307 LeuLysLysLeuAlaGluGluIleGluLysTyrLysThrPheSer

1261 ATTGATACGGAAACAACTTCACTTGATCCATTTGAAGCTAAACTG
 322 IleAspThrGluThrThrSerLeuAspProPheGluAlaLysLeu

1306 GTTGGGATCTCTATTTCCACAATGGAAGGGAAGGCGTATTATATT
 337 ValGlyIleSerIleSerThrMetGluGlyLysAlaTyrTyrIle

1351 CCGGTGTCTCATTTTGGAGCTAAGAATATTTCCAAAAGTTTAATA
 352 ProValSerHisPheGlyAlaLysAsnIleSerLysSerLeuIle

1396 GATAAATTTCTAAAACAAATTTTGCAAGAGAAGGATTATAATATC
 367 AspLysPheLeuLysGlnIleLeuGlnGluLysAspTyrAsnIle

1441 GTTGGTCAGAATTTAAAATTTGACTATGAGATTTTTAAAAGCATG
 382 ValGlyGlnAsnLeuLysPheAspTyrGluIlePheLysSerMet

1486 GGTTTTTCTCCAAATGTTCCGCATTTTGATACGATGATTGCAGCC
 397 GlyPheSerProAsnValProHisPheAspThrMetIleAlaAla

1531 TATCTTTTAAATCCAGATGAAAAACGTTTTAATCTTGAAGAGCTA
 412 TyrLeuLeuAsnProAspGluLysArgPheAsnLeuGluGluLeu

1576 TCCTTAAAATATTTAGGTTATAAAATGATCTCGTTTGATGAATTA
 427 SerLeuLysTyrLeuGlyTyrLysMetIleSerPheAspGluLeu

1621 GTAAATGAAAATGTACCATTGTTTGGAAATGACTTTTCGTATGTT
 442 ValAsnGluAsnValProLeuPheGlyAsnAspPheSerTyrVal

1666 CCACTAGAAAGAGCCGTTGAGTATTCCTGTGAAGATGCCGATGTG
 457 ProLeuGluArgAlaValGluTyrSerCysGluAspAlaAspVal

1711 ACATACAGAATATTTAGAAAGCTTGGTAGGAAGATATATGAAAAT
 472 ThrTyrArgIlePheArgLysLeuGlyArgLysIleTyrGluAsn

1756 GAGATGGAAAAGTTGTTTTACGAAATTGAGATGCCCTTAATTGAT
 487 GluMetGluLysLeuPheTyrGluIleGluMetProLeuIleAsp

1801 GTTCTTTCAGAAATGGAACTAAATGGAGTGTATTTTGATGAGGAA
 502 ValLeuSerGluMetGluLeuAsnGlyValTyrPheAspGluGlu

1846 TATTTAAAAGAATTATCAAAAAAATATCAAGAAAAAATGGATGGA
 517 TyrLeuLysGluLeuSerLysLysTyrGlnGluLysMetAspGly

1891 ATTAAGGAAAAGTTTTTGAGATAGCTGGTGAAACTTTCAATTTA
 532 IleLysGluLysValGluIleAlaGlyGluThrPheAsnLeu

1936 AACTCTTCAACTCAAGTAGCATATATACTATTTGAAAAATTAAAT
 547 AsnSerSerThrGlnValAlaTyrIleLeuPheGluLysLeuAsn
```

```
1981 ATTGCTCCTTACAAAAAAACAGCGACTGGTAAGTTTTCAACTAAT
 562 IleAlaProTyrLysLysThrAlaThrGlyLysPheSerThrAsn

2026 GCGGAAGTTTTAGAAGAACTTTCAAAAGAACATGAAATTGCAAAA
 577 AlaGluValLeuGluGluLeuSerLysGluHisGluIleAlaLys

2071 TTGTTGCTGGAGTATCGAAAGTATCAAAAATTAAAAAGTACATAT
 592 LeuLeuLeuGluTyrArgLysTyrGlnLysLeuLysSerThrTyr

2116 ATTGATTCAATACCGTTATCTATTAATCGAAAAACAAACAGGGTC
 607 IleAspSerIleProLeuSerIleAsnArgLysThrAsnArgVal

2161 CATACTACTTTTCATCAAACAGGAACTTCTACTGGAAGATTAAGT
 622 HisThrThrPheHisGlnThrGlyThrSerThrGlyArgLeuSer

2206 AGTTCAAATCCAAATTTGCAAAATCTTCCAACAAGAAGCGAAGAA
 637 SerSerAsnProAsnLeuGlnAsnLeuProThrArgSerGluGlu

2251 GGAAAAGAAATAAGAAAGCAGTAAGACCTCAAAGACAAGATTGG
 652 GlyLysGluIleArgLysAlaValArgProGlnArgGlnAspTrp

2296 TGGATTTTAGGTGCTGACTATTCTCAGATAGAACTAAGGGTTTTA
 667 TrpIleLeuGlyAlaAspTyrSerGlnIleGluLeuArgValLeu

2341 GCGCATGTAAGTAAAGATGAAAATCTACTTAAAGCATTTAAAGAA
 682 AlaHisValSerLysAspGluAsnLeuLeuLysAlaPheLysGlu

2386 GATTTAGATATTCATACAATTACTGCTGCCAAAATTTTTGGTGTT
 697 AspLeuAspIleHisThrIleThrAlaAlaLysIlePheGlyVal

2431 TCAGAGATGTTTGTTAGTGAACAAATGAGAAGAGTTGGAAAGATG
 712 SerGluMetPheValSerGluGlnMetArgArgValGlyLysMet

2476 GTAAATTTTGCAATTATTTATGGAGTTTCACCTTATGGTCTTTCA
 727 ValAsnPheAlaIleIleTyrGlyValSerProTyrGlyLeuSer

2521 AAGAGAATTGGTCTTAGTGTTTCAGAGACTAAAAAATAATAGAT
 742 LysArgIleGlyLeuSerValSerGluThrLysLysIleIleAsp

2566 AACTATTTTAGATACTATAAAGGAGTTTTTGAATAGGGAAAAAGG
 757 AsnTyrPheArgTyrTyrLysGlyValPheGluTyrLeuLysArg

2611 ATGAAAGATGAAGCAAGGAAAAAAGGTTATGTTACAACGCTTTTT
 772 MetLysAspGluAlaArgLysLysGlyTyrValThrThrLeuPhe

2656 GGAAGGCGCAGATATATTCCACAGTTAAGATCGAAAAATGGTAAT
 787 GlyArgArgArgTyrIleProGlnLeuArgSerLysAsnGlyAsn

2701 AGAGTTCAAGAAGGAGAAAGAATAGCTGTAAACACTCCAATTCAA
 802 ArgValGlnGluGlyGluArgIleAlaValAsnThrProIleGln

2746 GGAACAGCAGCTGATATAATAAAGATAGCTATGATTAATATTCAT
 817 GlyThrAlaAlaAspIleIleLysIleAlaMetIleAsnIleHis

2791 AATAGATTGAAGAAGGAAAATCTACGTTCAAAAATGATATTGCAG
 832 AsnArgLeuLysLysGluAsnLeuArgSerLysMetIleLeuGln

2836 GTTCATGACGAGTTAGTTTTTGAAGTGCCCGATAATGAACTGGAG
 847 ValHisAspGluLeuValPheGluValProAspAsnGluLeuGlu

2881 ATTGTAAAGATTTAGTAAGAGATGAGATGGAAAATGCAGTTAAG
 862 IleValLysAspLeuValArgAspGluMetGluAsnAlaValLys

2926 CTAGACGTTCCTTTAAAAGTAGATGTTTATTATGGAAAAGAGTGG
 877 LeuAspValProLeuLysValAspValTyrTyrGlyLysGluTrp

2971 GAATAATGGCTGGGGTAAAGGAATTTAAAGATCTAATAGAATTAA
 892 Glu

3016 ATGAATATGTTACAAAAAAAATAGAATTGACGGGTCTTACAAGTG

3061 AGACCTTTAGGTTTTATGCAGATGTTGTTAGAGCCAATAACCATT

3106 CTACAGGTTTGTATATTGATGTTTCACAACCTTATACTGCAAAGA

3151 ATGGAACAAGAAATATTGAAATTACTGTGTATGTACCTAGATATC

3196 TTGCACCAAAAATTTTGGAAGTTATAAAAGTTTCTAATGTTAAGG

3241 AACTTGTTGGGAAAAAATGGATTTTTCAAGGGAGACTTTCTTTTT

3286 TCAGAGATAGAATGAGTTTTACCTTCTATGCAGATACAATAGCTC

3331 CGATGGGAGAATCTGAGATTGAAAAAAGAAGAAAAGAAATATTGA

3376 AAGAGCTTGAGGTTAGAAATTTATTAATGAAAGAAAAGCATGATC

3421 TTTCTGAATTGCCACCAATAAAAAAGATTGCTATTATAACATCTA

3466 AAAGTGCAGCGGGTTACGAAGATTTTTTAAAAAACTTGACAGTTC

3511 ATTATTTGTACCGCCCTATTGTTCACCTTTATGAATCACCTATGC

3556 AAGGGGCACAGACTGCATCTGGTATTATTTTAGCGCTTAATCGTA

3601 TAAGAAAATCGAATATAGACTATGATGTTGTTGTTATTGCTCGTG

3646 GCGGTGGTGCAAGAAGCGATCTGATGTATTTTGATGATTTGTCAC

3691 TTGGAATAGAAATTGCAAAGTTTAATGAGTATTGTCCAATTTTAT

3736 CGGGCATAGGTCATGAAAGAGATTTTACAATTCCAGATTATGTTG

3781 CCTGGAAGAGATTTGCTACTCCGACAGAAGTTGCAAGAGCTATAT

3826 CAAAGCAAATAGAAGATAATGTGAAAAAATTGGATGATAGTTATA

3871 ATGACTTAAGGATTTTACTTTCTAATGTTTTTAAAATCTATGAGA

3916 GAACGGTAGAATTGGGTCTGATAGATTATATGAAGAAAGTTATAG

3961 GAAGCGATTTTATAAAGATAGTAAAAGATCTGGATGAAACTTATG

4006 AAAAGATTGAAAATTTTGTTAGTTACAAAATAAATGATTCATCTC

4051 AGAGACTATCTGAAGATTTTTTAAGGTTTATGTCTAATTCTCTTG

4096 AAAATAAGTTGAAATCCAAAAAGGACAGTGTTGAAAATTTTGAAA

4141 AAATACTTGAAAAAGATATATCAATTTTACTTTCAAATAAAGAGA

4186 CAATGCTTAATGAAACATTTCAGGAGCTTTTAAAACGAGAAGAAT

4231 TTGCACCACTTTTATTTGGTGGGGCATTGGTTATGAAAAGTGGAC

4267 ATTTTGTAAAA
```

The above nucleotide sequence was identified by a "degenerate primer" method that has broad utility and is an important aspect of the present invention. In the degenerate primer method, DNA fragments of any thermostable polymerase coding sequence corresponding to conserved domains of known thermostable DNA polymerases can be identified.

The degenerate primer method was developed by comparing the amino acid sequences of DNA polymerase proteins from Taq, Tth, T7, and *E. coli* in which various conserved regions were identified. Primers corresponding to these conserved regions were then designed. As a result of the present invention, Taf sequences can be used to design other degenerate primers, as can the coding sequences of the Thermus species sps17 DNA polymerase gene (see PCT Publication No. WO 92/06200, filed Sep. 30, 1991, and incorporated herein by reference) and the *Thermotoga maritima* DNA polymerase gene (see PCT Publication No. WO 92/03556, filed Aug. 13, 1991, and incorporated herein by reference), and the Thermus species Z05 DNA polymerase gene (see PCT Publication No. WO 92/06200, filed Sep. 30, 1991, and incorporated herein by reference). The generic utility of the degenerate primer process is exemplified herein by specific reference to the method as applied to cloning the Taf DNA polymerase gene.

To clone the Taf DNA polymerase gene, regions of conserved amino acid sequences of DNA polymerase enzymes were converted to all of the possible codons which represent each of the amino acids. Due to the degenerate nature of the genetic code, a given amino acid may be represented by several different codons. Where more than one base can be present in a codon for a given amino acid, the sequence is said to be degenerate.

The primers were then synthesized as a pool of all of the possible DNA sequences that could code for a given amino acid sequence. The amount of degeneracy of a given primer pool can be determined by multiplying the number of possible nucleotides at each position.

The greater the number of individual unique primer DNA sequences within a primer pool, the greater the probability that one of the unique primer sequences will bind to regions of the target chromosomal DNA other than the one desired; hence, the lesser the specificity of the resulting amplification. To increase the specificity of the amplification using degenerate primers, the pools are synthesized as subsets such that the entire group of subsets includes all possible DNA sequences encoding the given amino acid sequence, but each individual subset only includes a portion: for example, one pool may contain either a G or C at a certain position while another pool contains either an A or T at the same position. As described herein, these subpools are designated with a DG number (where number is between 99 and 200).

Both forward primers (directed from the 5' region toward the 3' region of the gene, complementary to the noncoding strand) and reverse primers (directed from the 3' region of the gene toward the 5' region of the gene, complementary to the coding strand) were designed for most of the conserved regions to clone Taf polymerase. The primers were designed with restriction sites at the 5' ends of the primers to facilitate cloning. The forward primers contained a BglII restriction site (AGATCT), while the reverse primers contained an EcoRI restriction site (GAATTC). In addition, the primers contained 2 additional nucleotides at the 5' end to increase the efficiency of cutting at the restriction site.

Degenerate primers were then used in PCR processes to amplify chromosomal DNA from Taf. The products of the PCR processes using a combination of forward and reverse primer pools in conjunction with a series of temperature profiles were compared. When specific products of similar size to the product gene rated using Taq chromosomal DNA were produced, the PCR fragments were gel purified, reamplified and cloned into the vector pBSM13+HindIII::BglII (a derivative of the Stratagene™ vector pBSM13+, now marketed as pBS+, in which the HindIII site of pBSM13+ was converted to a BglII site). The PCR fragments were cloned and sequenced; fragments were identified as potential thermostable DNA polymerase coding sequences if the fragments contained sequences that encode regions of amino acid homology to other known polymerase protein sequences, particularly those of Taq polymerase and Tth polymerase.

The portions of the Taf DNA polymerase gene were then identified in the chromosomal DNA of Taf by Southern blot analysis. The Taf chromosomal DNA was digested with a variety of enzymes and transferred to nitrocellulose filters. Probes labeled with $^{32}P$ or biotin-dUTP were generated for various regions of the gene from the cloned PCR products. The probes were hybridized to the nitrocellulose-bound genomic DNA, allowing identification of the molecular weight of the chromosomal DNA fragment hybridizing to the probe. The use of probes covering the 5' and 3' regions of the gene ensures that the DNA fragment(s) contain most if not all of the structural gene for the polymerase. Restriction enzymes can be identified that can be used to produce fragments that contain the structural gene in a single DNA fragment or in several DNA fragments to facilitate cloning.

Once identified, chromosomal DNA encoding portions of the Taf DNA polymerase gene was cloned. Chromosomal DNA was digested with the identified restriction enzymes, and size fractionated. Fractions containing the desired size range were concentrated, desalted, and cloned into the pBSM13+HindIII::BglII cloning vector. Clones were identified by hybridization using labeled probes generated from the previous cloned PCR products. The cloned fragments were identified by restriction enzyme analysis and Southern blot analysis.

The DNA sequence and amino acid sequence shown above and the DNA compounds that encode those sequences can be used to design and construct recombinant DNA expression vectors to express Taf DNA polymerase activity in a wide variety of host cells. A DNA compound encoding all or part of the DNA sequence shown above can also be used as a probe to identify thermostable polymerase-encoding DNA from other organisms, and the amino acid sequence shown above can be used to design peptides for use as immunogens to prepare antibodies that can be used to identify and purify a thermostable polymerase.

Whether produced by recombinant vectors that encode the above amino acid sequence or by native Taf cells, however, Taf DNA polymerase will typically be purified prior to use in a recombinant DNA technique. The present invention provides such purification methodology.

For recovering the native protein, the cells are grown using the method of Huber et al., 1989, *System App. Microbial.* 12:32–37. After cell growth, the isolation and purification of the enzyme takes place in six stages, each of which is carried out at a temperature below room temperature, preferably about 0° to about 4° C., unless stated otherwise.

In the first stage or step, the cells, if frozen, are thawed, disintegrated by ultrasound, suspended in a buffer at about pH 7.5, and centrifuged.

In the second stage, the supernatant is collected and then fractionated by adding a salt such as dry ammonium sulfate. The appropriate fraction (typically 45–75% of saturation) is collected, dissolved in a 0.2 M potassium phosphate buffer preferably at pH 6.5, and dialyzed against the same buffer.

The third step removes nucleic acids and some protein. The fraction from the second stage is applied to a DEAE-cellulose column equilibrated with the same buffer as used above. Then the column is washed with the same buffer and the flow-through protein-containing fractions, determined by absorbance at 280 nm, are collected and dialyzed against a 10 mM potassium phosphate buffer, preferably with the same ingredients as the first buffer, but at a pH of 7.5.

The fourth step consists of hydroxyapatite chromatography; the fraction so collected is applied to a hydroxyapatite column equilibrated with the buffer used for dialysis in the third step. The column is then washed and the enzyme eluted with a linear gradient of a buffer such as 0.01 M to 0.5 M potassium phosphate buffer at pH 7.5 containing 10 mM 2-mercaptoethanol and 5% glycerol. The pooled fractions containing thermostable DNA polymerase activity are dialyzed against the same buffer used for dialysis in the third step.

The fifth stage consists of anion exchange chromatography; the dialyzed fraction is applied to a DEAE-cellulose column, equilibrated with the buffer used for dialysis in the third step. The column is then washed and the enzyme eluted with a linear gradient of a buffer such as 0.01 to 0.6 M KCl in the buffer used for dialysis in the third step. Fractions with thermostable enzyme activity are then tested for contaminating deoxyribonucleases (endo- and exonucleases) using any suitable procedure. For example, the endonuclease activity may be determined electrophoretically from the change in molecular weight of phage lambda DNA or supercoiled plasmid DNA after incubation with an excess of DNA polymerase. Similarly, exonuclease activity may be determined electrophoretically from the change in molecular weight of restriction enzyme-cleaved DNA after treatment with the DNA polymerase fraction. The fractions determined to have polymerase activity but no deoxyribonuclease activity are pooled and dialyzed against the same buffer used in the third step.

The sixth step consists of DNA binding protein affinity chromatography; the pooled fractions are placed on a phosphocellulose column with a set bed volume. The column is washed and the enzyme eluted with a linear gradient of a buffer such as 0.01 to 0.8 M KCl in a potassium phosphate buffer at pH 7.5. The pooled fractions having thermostable polymerase activity and no deoxyribonuclease activity are dialyzed against a buffer at pH 8.0.

The molecular weight of the DNA polymerase purified from Taf may be determined by any technique, for example, by SDS-PAGE analysis using protein molecular weight markers. The molecular weight, calculated from the coding sequence, of Taf DNA polymerase is 103,273 daltons. The purification protocol of native Taf DNA polymerase is described in detail in Example 1. Purification of the recombinant Taf polymerase of the invention can be carried out with similar methodology.

The entire coding sequence of the Taf DNA polymerase gene is not required, however, to produce a biologically active gene product with DNA polymerase activity. The availability of DNA encoding the Taf DNA polymerase sequence provides the opportunity to modify the coding sequence so as to generate mutein (mutant protein) forms also having DNA polymerase activity. The amino(N)-terminal portion of the Taf polymerase is not believed to be necessary for polymerase activity. Using recombinant DNA methodology, one can delete up to approximately one-third of the N-terminal coding sequence of the Taf gene, clone, and express a gene product that is quite active in polymerase assays. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain of Taf polymerase may be modified by oxidation, reduction, or other derivation, and the protein may be cleaved to obtain fragments that retain activity. Such alterations that do not destroy activity do not remove the protein from the definition of a protein with Taf polymerase activity and so are specifically included within the scope of the present invention.

Modifications to the primary structure of the Taf DNA polymerase gene by deletion, addition, or alteration so as to change the amino acids incorporated into the Taf DNA polymerase during translation can be made without destroying the high temperature DNA polymerase activity of the protein. Such substitutions or other alterations result in the production of proteins having an amino acid sequence encoded by DNA falling within the contemplated scope of the present invention. Likewise, the cloned genomic sequence, or homologous synthetic sequences, of the Taf DNA polymerase gene can be used to express a fusion polypeptide with Taf DNA polymerase activity or to express a protein with an amino acid sequence identical to that of native Taf DNA polymerase. In addition, such expression can be directed by a control sequence that functions in whatever host is chosen to express the Taf DNA polymerase.

Thus, the present invention provides a coding sequence for Taf DNA polymerase from which expression vectors applicable to a variety of host systems can be constructed and the coding sequence expressed. Portions of the Taf polymerase-encoding sequence are also useful as probes to retrieve other thermostable polymerase-encoding sequences in a variety of species. Accordingly, oligonucleotide probes that encode at least four to six amino acids can be synthesized and used to retrieve additional DNAs encoding a thermostable polymerase. Because there may not be an exact match between the nucleotide sequence of the thermostable DNA polymerase gene of Taf and the corresponding gene of other species, oligomers containing approximately 12–18 nucleotides (encoding the four to six amino sequence) are usually necessary to obtain hybridization under conditions of sufficient stringency to eliminate false positives. Sequences encoding six amino acids supply ample information for such probes.

The present invention, by providing coding sequences and amino acid sequences for Taf DNA polymerase, therefore enables the isolation of other thermostable polymerase enzymes and the coding sequences for those enzymes. The deduced amino acid sequence of the Taf DNA polymerase protein is similar to the amino acid sequences for other thermostable DNA polymerases, such as those from Taq and Tth (see PCT Publication No. 91/09950, incorporated herein by reference).

However, regions of dissimilarity between the coding sequences of the thermostable DNA polymerases can also be used as probes to identify other thermostable polymerase coding sequences which encode enzymes having some properties of one known thermostable polymerase and perhaps different properties. For example, the coding sequence for a thermostable polymerase having some properties of Taq and other divergent properties of Taf may be identified by using probes comprising regions of dissimilarity between Taq and Taf.

Whether one desires to produce an enzyme identical to native Taf DNA polymerase or a derivative or homologue of that enzyme, the production of a recombinant form of Taf polymerase typically involves the construction of an expression vector, the transformation of a host cell with the vector, and culture of the transformed host cell under conditions such that expression will occur.

To construct the expression vector, a DNA is obtained that encodes the mature (used here to include all muteins) enzyme or a fusion of the Taf polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant Taf polymerase. The Taf polymerase is isolated from the medium or from the cells, although recovery and purification of the protein may not be necessary in some instances.

Each of the foregoing steps can be done in a variety of ways. For example, the desired coding sequence may be obtained from genomic fragments and used directly in appropriate hosts. The construction of expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with the suitable restriction enzyme (or enzymes) under conditions that are generally understood in the art and specified by the manufacturers of commercially available restriction enzymes. See, e.g., New England Biolabs, Product Catalog. In general, about 1 $\mu$g of plasmid or other DNA is cleaved by one unit of enzyme in about 20 $\mu$l of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., *Methods in Enzymology*, 1980, 65:499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° C. to 25° C. in 50 mM Tris, pH 7.6, 50 mM NaCl, 10 mM MgCl$_2$, 10 mM DTT, and 5 to 10 $\mu$M dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Synthetic oligonucleotides can be prepared using the triester method of Matteucci et al., 1981, *J. Am. Chem. Soc.* 103:3185–3191, or automated synthesis methods. Kinasing of single strands prior to annealing or for labeling is achieved using an excess, e.g., approximately 10 units, of polynucleotide kinase to 0.5 $\mu$M substrate in the presence of 50 mM Tris, pH 7.6, 10 mM MgCl$_2$, 5 mM dithiothreitol (DTT), and 1 to 2 $\mu$M ATP. If kinasing is for labeling of probe, the ATP will be labeled with $^{32}$P.

Ligations are performed in 15–30 $\mu$l volumes under the following standard conditions and temperatures: 20 mM Tris-Cl, pH 7.5, 10 mM MgCl$_2$, 10 mM DTT, 33 $\mu$g/ml BSA, 10 mM–50 mM NaCl, and either 40 $\mu$M ATP and 0.01–0.02 (Weiss) units T4 DNA ligase at 0° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 $\mu$g/ml total DNA concentrations (5–100 nM total ends concentration). Intermolecular blunt end ligations (usually employing a 20–30 fold molar excess of linkers, optionally) are performed at 1 $\mu$M total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove the phosphatase and purify the DNA. Alternatively, religation of unwanted vector fragments can be prevented by restriction enzyme digestion before or after ligation, if appropriate restriction sites are available.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in of a single-stranded vector, such as pBSM13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

In the construction set forth below, correct ligations for plasmid construction are confirmed by first transforming *E. coli* strain DG101 (ATCC 47043) or another suitable host with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al, 1969, *Proc. Natl. Acad. Sci.* U.S.A. 62:1159, optionally following chloramphenicol amplification (Clewell, 1972, *J. Bacteriol.* 110:667). Another method for obtaining plasmid DNA is described as the "Base-Acid" extraction method at page 11 of the Bethesda Research Laboratories publication *Focus*, volume 5, number 2, and very pure plasmid DNA can be obtained by replacing steps 12 through 17 of the protocol with CsCl/ ethidium bromide ultracentrifugation of the DNA. The isolated DNA is analyzed by restriction enzyme digestion and/or sequenced by the dideoxy method of Sanger et al., 1977, *Proc. Natl. Acad. Sci.* U.S.A. 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of Taf polymerase.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ or $P_L T_{7RBS}$ control sequence, *E. coli* K12 strain MC1000 lambda lysogen, $\lambda N_7 N_{53} CI857\ SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of Taf DNA polymerase. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six bp 3' of the $N_{RBS}$ sequence. Also useful is the phosphatase A (phoA) system described by Chang et al. in European Patent Publication No. 196,864, published Oct. 8, 1986. However, any available promoter system compatible with procaryotes can be used to construct a Taf expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme Reg.* 7:149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast Taf expression vectors.

The Taf gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986), Setlow et al., eds., Plenum Publishing, Vol. 8, pp. 277–297). Insect cell-based expression can be accomplished in *Spodoptera frugipeida*. These systems are also successful in producing recombinant Taf polymerase.

Depending on the host cell used, transformation is done using standard techniques appropriate to such cells. The calcium treatment employing calcium chloride, as described by Cohen, 1972, *Proc. Natl Acad. Sci.* U.S.A. 69:2110 is used for procaryotes or other cells that contain substantial cell wall barriers. Infection with *Agrobacterium tumefaciens* (Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946, and Hsiao et al., 1979, *Proc. Natl. Acad. Sci.* U.S.A. 76:3829.

Once the Taf DNA polymerase has been expressed in a recombinant host cell, purification of the protein may be desired. Although a variety of purification procedures can be used to purify the recombinant thermostable polymerase of the invention, fewer steps may be necessary to yield an enzyme preparation of equal purity. Because *E. coli* host proteins are heat-sensitive, the recombinant thermostable Taf DNA polymerase can be substantially enriched by heat inactivating the crude lysate. This step is done in the presence of a sufficient amount of salt (typically 0.3M ammonium sulfate) to ensure dissociation of the Taf DNA polymerase from the host DNA and to reduce ionic interactions of Taf DNA polymerase with other cell lysate proteins.

In addition, the presence of 0.3M ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture (containing either native or recombinant Taf DNA polymerase) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used which contains, for example, greater than or equal to 0.3M ammonium sulfate. The column and the sample are adjusted to 0.3M ammonium sulfate in 50 mM Tris (pH 7.5) and 5 mM EDTA ("TE") buffer that also contains 0.5 mM DTT, and the sample is applied to the column. The column is washed with the 0.3M ammonium sulfate buffer. The enzyme may then be eluted with solvents which attenuate hydrophobic interactions, such as decreasing salt gradients, or increasing gradients or addition of ethylene or propylene glycol, or urea. For native Taf DNA polymerase, a preferred embodiment involves washing the column with 2M urea in 20% ethylene glycol in TE-DTT wash.

For long-term stability, Taf DNA polymerase enzyme can be stored in a buffer that contains one or more non-ionic polymeric detergents. Such detergents are generally those that have a molecular weight in the range of approximately 100 to 250,000 daltons, preferably about 4,000 to 200,000 daltons and stabilize the enzyme at a pH of from about 3.5 to about 9.5, preferably from about 4 to 8.5. Examples of such detergents include those specified on pages 295–298 of McCutcheon's *Emulsifiers & Detergents,* North American edition (1983), published by the McCutcheon Division of MC Publishing Co., 175 Rock Road, Glen Rock, N.J. (U.S.A.).

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol NP-40, an ethoxylated alkyl phenol(nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. No. 4,683,202, issued Jul. 28, 1987, the disclosure of which is incorporated herein by reference. The PCR nucleic acid amplification method involves amplifying at least one specific nucleic acid sequence contained in a nucleic acid or a mixture of nucleic acids and in the most common embodiment, produces double-stranded DNA.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:

(a) contacting each nucleic acid strand with four different nucleoside triphosphates and one oligonucleotide primer for each strand of the specific sequence being amplified, wherein each primer is selected to be substantially complementary to the different strands of the specific sequence, such that the extension product synthesized from one primer, when it is separated from its complement, can serve as a template for synthesis of the extension product of the other primer, said contacting being at a temperature which allows hybridization of each primer to a complementary nucleic acid strand;

(b) contacting each nucleic acid strand; at the same time as or after step (a), with a DNA polymerase from Taf which enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer which is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)–(f) are repeated until the desired level of amplification is obtained.

The amplification method is useful not only for producing large amounts of a specific nucleic acid sequence of known sequence but also for producing nucleic acid sequences which are known to exist but are not completely specified. One need know only a sufficient number of bases at both ends of the sequence in sufficient detail so that two oligonucleotide primers can be prepared which will hybridize to different strands of the desired sequence at relative positions along the sequence such that an extension product synthesized from one primer, when separated from the template (complement), can serve as a template for extension of the other primer. The greater the knowledge about the bases at both ends of the sequence, the greater can be the specificity of the primers for the target nucleic acid sequence.

In any case, an initial copy of the sequence to be amplified must be available, although the sequence need not be pure or a discrete molecule. In general, the amplification process involves a chain reaction for producing at least one specific nucleic acid sequence, called the "target" sequence, given that (a) the ends of the target sequence are known in sufficient detail that oligonucleotides can be synthesized which will hybridize to them, and (b) a small amount of the sequence is available to initiate the chain reaction. The product accumulates exponentially relative to the number of reaction steps involved. The product of the chain reaction is a discrete nucleic duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, from natural DNA or RNA from any source, including bacteria, yeast, viruses, organelles, and higher organisms such as plants and animals, or from preparations of nucleic acid made in vitro. DNA or RNA may be extracted from blood, tissue material such as chorionic villi, or amniotic cells by a variety of techniques. See, e.g., Maniatis et al., 1982, *Molecular Cloning: A Laboratory Manual* (Cold Spring Harbor Laboratory, Cold Spring Harbor, N.Y.) pp. 280–281. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids can also be employed as can nucleic acids produced from a previous amplification reaction (using the same or different primers). The specific nucleic acid sequence to be amplified may be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki et al., 1985, *Science* 230:1530–1534) or a portion of a nucleic acid sequence due to a particular microorganism, which organism might constitute only a very minor fraction of a particular biological sample. The cells can be directly used in the amplification process after suspension in hypoionic buffer and heat treatment at about 90°–100° C. until cell lysis and dispersion of intracellular components occur (generally 1 to 15 minutes). After the heating step, the amplification reagents may be added directly to the lysed cells. The starting nucleic acid sequence may contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. A least one primer from this collection will be sufficiently homologous with the end of the desired sequence to be amplified to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process. When allelic variants or different members of a multigene family are to be amplified, however, one can often amplify several different sequences with a single set of primers.

A sequence within a given sequence can be amplified after a given number of amplifications to obtain greater specificity of the reaction by adding after at least one cycle of amplification a set of primers that are complementary to internal sequences (that are not on the ends) of the sequence to be amplified. Such primers may be added at any stage and will provide a shorter amplified fragment. Alternatively, a longer fragment can be prepared by using primers with non-complementary 5' ends but having some 3' overlap with the 5' ends of the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. Although the initial cycles may be somewhat inefficient, due to the mismatch between the mutagenic primer and the target, in further cycles the mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods or automated embodiments thereof. The phosphotriester method is described in Narang et al., 1979, *Meth. Enzymol.* 68:90, and U.S. Pat. No. 4,356,270. The phosphodiester method is described in Brown et al., 1979, *Meth. Enzymol.* 68:109. In one such automated embodiment, diethylphosphoramidites are used as starting materials and may be synthesized as described by Beaucage et al., 1981, *Tetrahedron Letters* 22:1859–1862. One method for synthesizing oligonucleotides on a modified solid support is described in U.S. Pat. No. 4,458,066. One can also use a primer that has been isolated from a biological source (such as a restriction endonuclease digest).

To produce a specific nucleic acid sequence using PCR, a nucleic acid containing that sequence is used as a template. The first step involves contacting each nucleic acid strand with four different nucleoside triphosphates and one oligonucleotide primer for each strand of each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. The concentration of nucleoside triphosphates can vary widely. Typically the concentration is 50–200 $\mu$M of each dNTP in the buffer for amplification, and $MgCl_2$ is present in the buffer in an amount of 1 to 3 mM to activate the polymerase and increase the specificity of the reaction. However, dNTP concentrations of 1–20 $\mu$M may be preferred for some applications, such as DNA sequencing or labeling PCR products at high specific activity.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of about 1000:1 are generally employed for cloned DNA templates, and primer:template ratios of about $10^8$:1 are generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed, and the reaction mixture is held at a temperature which promotes hybridization of the primer to its complementary target (template) sequence. Such temperature is generally from about 35° C. to 65° C. or more, preferably about 37°–60° C. for an effective time, generally from a few seconds to five minutes, preferably from 30 seconds to one minute. A hybridization temperature of 35–80° C. may be used for Taf DNA polymerase, and 15-mer or longer primers are used to increase the specificity of primer hybridization. Shorter primers require lower hybridization temperatures or agents which stabilize double-stranded DNA.

The complement to the original single-stranded nucleic acids can be synthesized by adding Taf DNA polymerase in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending where the primer hybridizes on the template), which may then be separated into single strands as described above to produce two single, separated, complementary strands. Alternatively, two or more appropriate primers (one of which will prime synthesis using the extension product of the other primer as a template) may be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 90° to 105° C. for times generally ranging from about a few seconds to 4 minutes, depending on the composition and size of the nucleic acid. Preferably, the effective denaturing temperature is 90°–100° C. for a few seconds to 1 minute. Strand separation may also be induced by an enzyme from the class of enzymes known as helicases or the enzyme RecA, which has helicase activity and in the presence of ATP is known to denature DNA. The reaction conditions suitable for separating the strands of nucleic acids with helicases are described by Kuhn Hoffmann-Berling, 1978, *CSH-Quantitative Biology* 43:63, and techniques for using RecA are reviewed in Radding, 1982, *Ann. Rev. Genetics* 16:405–437. The denaturation produces two separated complementary strands of equal or unequal length.

If the double-stranded nucleic acid is denatured by heat, the reaction mixture is allowed to cool to a temperature which promotes hybridization of each primer to the complementary target (template) sequence. This temperature is usually from about 35° C. to 65° C. or more, depending on reagents, preferably 37°–60° C. The hybridization temperature is maintained for an effective time, generally 30 seconds to 5 minutes, and preferably 1–3 minutes. In practical terms, the temperature is simply lowered from about 95° C. to as low as 37° C., and hybridization occurs at a temperature within this range.

Whether the nucleic acid is single- or double-stranded, the DNA polymerase from Taf may be added at the denaturation step or when the temperature is being reduced to or is in the range for promoting hybridization. Although the thermostability of Taf polymerase allows one to add Taf polymerase to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80°–90° C.).

Depending on the nucleic acid(s) employed, the typical temperature effective for this synthesis reaction generally ranges from about 40° to 80° C., preferably 50°–75° C. The temperature more preferably ranges from about 65°–75° C. for Taf DNA polymerase. The period of time required for this synthesis may range from several seconds to 40 minutes or more, depending mainly on the temperature, the length of the nucleic acid, the enzyme, and the complexity of the nucleic acid mixture. The extension time is usually about 30 seconds to three minutes. If the nucleic acid is longer, a longer time period is generally required for complementary strand synthesis. The newly synthesized strand and the complement nucleic acid strand form a double-stranded molecule which is used in the succeeding steps of the amplification process.

In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level which promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50°–70° C.

The heating and cooling steps involved in one cycle of strand separation, hybridization, and extension product synthesis can be repeated as often as needed to produce the desired quantity of the specific nucleic acid sequence. The only limitation is the amount of the primers, thermostable enzyme, and nucleoside triphosphates present. Usually, from 15 to 30 cycles are completed. For diagnostic detection of amplified DNA, the number of cycles will depend on the nature of the sample and the sensitivity of the detection process used after amplification. If the sample is a complex mixture of nucleic acids, more cycles will usually be required to amplify the signal sufficiently for detection. For general amplification and detection, the process is repeated about 15 times. When amplification is used to generate sequences to be detected with labeled sequence-specific probes and when human genomic DNA is the target of amplification, the process is usually repeated 15 to 30 times to amplify the sequence sufficiently that a clearly detectable signal is produced, i.e., so that background noise does not interfere with detection.

No additional nucleotides, primers, or thermostable enzyme need be added after the initial addition, provided that no key reagent has been exhausted and that the enzyme has not become denatured or irreversibly inactivated, in which case additional polymerase or other reagent would have to be added for the reaction to continue. After the appropriate number of cycles has been completed to produce the desired amount of the specific nucleic acid sequence, the reaction may be halted in the usual manner, e.g., by inactivating the enzyme by adding EDTA, phenol, SDS, or $CHCl_3$ or by separating the components of the reaction.

The amplification process may be conducted continuously. In one embodiment of an automated process, the reaction mixture may be temperature cycled such that the temperature is programmed to be controlled at a certain level for a certain time. One such instrument for this purpose is the automated machine for handling the amplification reaction developed and marketed by Perkin-Elmer Cetus Instruments. Detailed instructions for carrying out PCR with the instrument are available upon purchase of the instrument.

Taf DNA polymerase is very useful in the diverse processes in which amplification of a nucleic acid sequence by the polymerase chain reaction is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers or amplified target sequences. Other processes suitable for Taf polymerase include those described in U.S. Pat. Nos. 4,683,194; 4,683,195; and 4,683,202 and European Patent Publication Nos. 229,701; 237,362; and 258,017; these patents and publications are incorporated herein by reference. In addition, the present enzyme is useful in asymmetric PCR (see Gyllensten and Erlich, 1988, *Proc. Natl. Acad. Sci. USA* 85:7652–7656, incorporated herein by reference); inverse PCR (Ochman et al., 1988, *Genetics* 120:621, incorporated herein by reference); and for DNA sequencing (see Innis et al., 1988, *Proc. Natl. Acad. Sci. USA* 85:9436–9440, and McConlogue et al., 1988, *Nuc. Acids Res.* 16(20):9869). Taf polymerase is also believed to have reverse transcriptase activity, (see PCT publication WO 91/0994, which is incorporated herein by reference), and 5'→3' exonuclease activity (also known as structure dependent single strand endonuclease (SDSSE) activity).

The reverse transcriptase activity of the Taf DNA polymerase permits this enzyme to be used in methods for transcribing and amplifying RNA. The improvement of such methods resides in the use of a single enzyme, whereas previous methods have required more than one enzyme.

The improved methods comprise the steps of: (a) combining an RNA template with a suitable primer under conditions whereby the primer will anneal to the corresponding RNA template; and (b) reverse transcribing the RNA template by incubating the annealed primer-RNA template mixture with Taf DNA polymerase under conditions sufficient for the DNA polymerase to catalyze the polymerization of deoxyribonucleotide triphosphates to form a DNA sequence complementary to the sequence of the RNA template.

In another aspect of the above method, the primer which anneals to the RNA template may also be suitable for use in a PCR amplification. In PCR, a second primer which is complementary to the reverse transcribed cDNA strand provides a site for initiation of synthesis of an extension product. As already discussed above, the Taf DNA polymerase is able to catalyze this extension reaction on the cDNA template.

In the amplification of an RNA molecule by Taf DNA polymerase, the first extension reaction is reverse transcription, and a DNA strand is produced as an RNA/cDNA hybrid molecule. The second extension reaction, using the DNA strand as a template, produces a double-stranded DNA molecule. Thus, synthesis of a complementary DNA strand from an RNA template with Taf DNA polymerase provides the starting material for amplification by PCR.

When Taf DNA polymerase is used for reverse transcription from an RNA template, buffers which contain $Mn^{2+}$ may provide improved stimulation of Taf reverse transcriptase activity compared to $Mg^{2+}$—containing reverse transcription buffers. Consequently, increased cDNA yields may also result from these methods.

As stated above, the product of RNA reverse transcription by Taf DNA polymerase is an RNA/cDNA hybrid molecule. The RNA can be removed or separated from the cDNA by heat denaturation or any number of other known methods including alkali, heat or enzyme treatment. The remaining cDNA strand then serves as a template for polymerization of a complementary strand, thereby providing a means for obtaining a double-stranded cDNA molecule suitable for amplification or other manipulation. The second strand synthesis requires a sequence specific primer and Taf DNA polymerase.

Following the synthesis of the second cDNA strand, the resultant double-stranded cDNA molecule can serve a number of purposes including DNA sequencing, amplification by PCR or detection of a specific nucleic acid sequence. Specific primers useful for amplification of a segment of the cDNA can be added subsequent to the reverse transcription. Also, it may be desirable to use a first set of primers to synthesize a specific cDNA molecule and a second nested set of primers to amplify a desired cDNA segment. All of these reactions are catalyzed by Taf DNA polymerase.

Taf DNA polymerase may also be used to simplify and improve methods for detection of RNA target molecules in a sample. In these methods, Taf DNA polymerase catalyzes: (a) reverse transcription; (b) second strand cDNA synthesis; and, if desired (c) amplification by PCR. The use of Taf DNA polymerase in the described methods eliminates the previous requirement of two sets of incubation conditions which were necessary due to the use of different enzymes for each step. The use of Taf DNA polymerase provides RNA reverse transcription and amplification of the resulting complementary DNA with enhanced specificity and with fewer steps than previous RNA cloning and diagnostic methods. These methods are adaptable for use in laboratory or clinical analysis, and kits for making such analysis simple to perform are an important aspect of the present invention.

The RNA which is reverse transcribed and amplified in the above methods can be derived from a number of sources. The RNA template may be contained within a nucleic acid preparation from an organism such as a viral or bacterial nucleic acid preparation. The preparation may contain cell debris and other components, purified total RNA or purified mRNA. The RNA template may also be a population of heterogeneous RNA molecules in a sample. Furthermore, the target RNA may be contained in a biological sample, and the sample may be a heterogeneous sample in which RNA is but a small portion thereof. Examples of such biological samples include blood samples and biopsied tissue samples.

Although the primers used in the reverse transcription step of the above methods are generally completely complementary to the RNA template, they need not be. As in PCR, not every nucleotide of the primer must be complementary to the template for reverse transcription to occur. For example, a non-complementary nucleotide sequence may be present at the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

The structure dependent single stranded endonuclease (SDSSE) activity of Taf DNA polymerase may limit the amount of product produced by PCR, thus creating a plateau phenomenon in the normally exponential accumulation of product. The SDSSE activity may also limit the size of the PCR product produced and the ability to generate PCR product from GC-rich target template. However, SDSSE activity can also be helpful; see International Publication No. WO 92/02638, based on PCT Application No. 91/05591, filed Aug. 6, 1991, and incorporated herein by reference. SDSSE activity relates to the hydrolysis of phosphodiester bonds. SDSSE activity generally excises 5' terminal regions of double-stranded DNA, thereby releasing 5'-mono- and oligonucleotides. The preferred substrate for the SDSSE activity is displaced single-stranded DNA, with hydrolysis of the phosphodiester bond which occurs between the displaced single-stranded DNA and the double-stranded DNA. The cleavage site is a phosphodiester bond in the double-stranded region.

Site-directed mutagenesis or deletion mutagenesis may be utilized to eliminate the SDSSE activity of a polymerase having such activity. For example, a site-directed mutation of G to A in the second position of the codon for Gly at residue 46 in the Taq DNA polymerase coding sequence has been found to result in an approximately >1,000- fold reduction of SDSSE activity in the protein encoded by the sequence with no apparent change in polymerase activity, processivity or extension rate. This site-directed mutation of the Taq DNA polymerase nucleotide sequence results in an amino acid change of Gly (46) to Asp. Glycine 46 is conserved in *Thermosipho africanus* DNA polymerase, but is present at codon 37, and the same Gly to Asp mutation would have a similar effect on Taf SDSSE activity.

Gly 46 is found in a conserved AVYGF sequence domain in Taq DNA polymerase; the sequence AVYGL contains the Gly (37) of Taf DNA polymerase. Changing the glycine to aspartic acid within this conserved sequence domain will reduce or eliminate the SDSSE activity. In addition, a deletion of all amino terminal amino acids up to and including the glycine in the AVYGF/L domain will also reduce or eliminate the SDSSE activity of any thermostable DNA polymerase having this sequence domain, including the DNA polymerase of Taf.

One property found in the Taf DNA polymerase, but lacking in native Taq DNA polymerase and native Tth DNA polymerase, is 3'→5' exonuclease activity. This 3'→5' exonuclease activity is generally considered desirable in certain applications, because misincorporated or unmatched bases of the synthesized nucleic acid sequence are eliminated by this activity. Therefore, the fidelity of PCR utilizing a polymerase with 3'→5' exonuclease activity (e.g. Taf DNA polymerase) may be increased. The 3'→5' exonuclease activity found in Taf DNA polymerase also decreases the probability of the formation of primer/dimer complexes in PCR. The 3'→5' exonuclease activity in effect prevents any extra dNTPs from attaching to the 3' end of the primer in a non-template dependent fashion by removing any nucleotide that is attached in a non-template dependent fashion. The 3'→5' exonuclease activity can eliminate single-stranded DNAs, such as primers or single-stranded template. In essence, every 3'-nucleotide of a single-stranded primer or template is treated by the enzyme as unmatched and is therefore degraded. To avoid primer degradation in PCR, one can add phosphorothioate to the 3' ends of the primers. Phosphorothioate modified nucleotides are more resistant to removal by 3'→5' exonucleases.

"Domain shuffling" or construction of "thermostable chimeric DNA polymerases" may be used to provide thermostable DNA polymerases containing novel properties. For example, substitution of the Taf DNA polymerase coding sequence comprising the 3'→5' exonuclease domain for the *Thermus aquaticus* DNA polymerase codons 289–422 would yield a novel thermostable DNA polymerase containing the 5'→3' exonuclease domain of Taq DNA polymerase (1–289), the 3'→5' exonuclease domain of Taf DNA polymerase, and the DNA polymerase domain of Taq DNA polymerase (423–832). Alternatively, the 5'→3' exonuclease domain and the 3'→5' exonuclease domain of Taf DNA polymerase may be fused to the DNA polymerase (dNTP binding and primer/template binding domains) portions of Taq DNA polymerase (ca. codons 423–832). The donors and recipients need not be limited to Taq and Taf DNA polymerases. Tth DNA polymerase provides analogous domains as Taq DNA polymerase. In addition, the enhanced/preferred reverse transcriptase properties of Tth DNA polymerase can be further enhanced by the addition of a 3'→5' exonuclease domain as illustrated above.

While any of a variety of means may be used to generate chimeric DNA polymerase coding sequences (possessing novel properties), a preferred method employs "overlap" PCR. In this method, the intended junction sequence is designed into the PCR primers (at their 5'-ends). Following the initial amplification of the individual domains, the various products are diluted (ca. 100 to 1000-fold) and combined, denatured, annealed, extended, and then the final forward and reverse primers are added for an otherwise standard PCR.

Thus, the sequence that codes for the 3'→5' exonuclease activity of Taf DNA polymerase can be removed from Taf DNA polymerase or added to other polymerases which lack this activity by recombinant DNA methodology. One can even replace, in a non-thermostable DNA polymerase, the 3'→5' exonuclease activity domain with the thermostable 3'→5' exonuclease domain of Taf polymerase. Likewise, the 3'→5' exonuclease activity domain of a non-thermostable DNA polymerase can be used to replace the 3'→5' exonuclease domain of Taf polymerase (or any other thermostable polymerase) to create a useful polymerase of the invention. Those of skill in the art recognize that the above chimeric polymerases are most easily constructed by recombinant DNA techniques. Similar chimeric polymerases can be constructed by deleting or by moving the 5'→3' exonuclease domain of one DNA polymerase to another.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE 1

Purification of *Thermosipho africanus* (Taf) DNA Polymerase

This example describes the isolation of Taf DNA polymerase from Taf.

Taf cells are grown by the method of Huber et al., supra. The culture of the Taf cells is harvested by centrifugation after cultivation, in late log phase, at a cell density of 0.2 g to 0.3 g wet weight/l. Twenty grams of cells are resuspended in 80 ml of a buffer consisting of 50 mM Tris HCl pH 7.5, 0.1 mM EDTA. The cells are lysed and the lysate is centrifuged for two hours at 35,000 rpm in a Beckman TI 45 rotor at 4° C. The supernatant is collected (fraction A) and the protein fraction precipitating between 45 and 75% saturation of ammonium sulfate is collected, dissolved in a buffer consisting of 0.2 M potassium phosphate buffer, pH 6.5, 10 mM 2-mercaptoethanol, and 5% glycerol, and finally dialyzed against the same buffer to yield fraction B.

Fraction B is applied to a 2.2×30 cm column of DEAE-cellulose, equilibrated with the above described buffer. The column is then washed with the same buffer and the fractions containing protein (determined by absorbance at 280 nM) are collected. The combined protein fraction is dialyzed against a second buffer, containing 0.01 M potassium phosphate buffer, pH 7.5, 10 mM 2-mercaptoethanol, and 5% glycerol, to yield fraction C.

Fraction C is applied to a 2.6×21 cm column of hydroxyapatite, equilibrated with the second buffer. The column is then washed and the enzyme is eluted with a linear gradient of 0.01–0.5 M potassium phosphate buffer, pH 7.5, containing 10 mM 2-mercaptoethanol and 5% glycerol. Fractions containing DNA polymerase activity are combined, concentrated four-fold using an Amicon stirred cell and YM10 membrane, and dialyzed against the second buffer to yield fraction D.

Fraction D is applied to a 1.6×28 cm column of DEAE-cellulose, equilibrated with the second buffer. The column is washed and the polymerase is eluted with a linear gradient of 0.01–0.5 M potassium phosphate in the second buffer. The fractions are assayed for contaminating endonuclease(s) and non-specific exonuclease(s) by electrophoretically detecting the change in molecular weight of phage λ DNA or supercoiled plasmid DNA after incubation with an excess of DNA polymerase (for endonuclease) and after treatment of restriction enzyme cleaved DNA with the DNA polymerase fractions (for exonuclease). Only those DNA polymerase fractions having minimal non-specific nuclease contamination are pooled. To the pool is added autoclaved gelatin in an amount of 250 µg/ml, and dialysis is conducted against the second buffer to yield Fraction E.

Fraction E is applied to a phosphocellulose column and eluted with a 100 ml gradient (0.01–0.8 M KCl gradient in 20 mM potassium phosphate buffer pH 7.5). The fractions are assayed for contaminating endo/exonuclease(s) as described above as well as for polymerase activity (by the method of Kaledin et al.) and then pooled. The pooled fractions are dialyzed against the second buffer, and then concentrated by dialysis against 50% glycerol and the second buffer to yield the desired ~100 kilodalton polymerase.

EXAMPLE 2

Degenerate PCR Priming

Table 1 provides a list of primers used in Examples 2 and 3 along with the sequence identification number for each.

Throughout the examples, A is Adenine; C is Cytidine; G is Guanidine; T is Thymidine; Y is C+T (pYrimidine); S is G+C (Strong interaction; three hydrogen bonds); W is A+T (Weak interaction; two hydrogen bonds); N is A+C+G+T (aNy); and R is G+A (puRine).

TABLE 1

Primer Sequences

| | | |
|---|---|---|
| DG144 | SEQ ID NO: 3 | 5'-CGGAATTCCNGGYARRTTATC |
| DG145 | SEQ ID NO: 4 | 5'-CGGAATTCCNGGYARRTTGTC |
| DG146 | SEQ ID NO: 5 | 5'-CGGAATTCCNGGRAGRTTATC |
| DG147 | SEQ ID NO: 6 | 5'-CGGAATTCCNGGRAGRTTGTC |
| DG148 | SEQ ID NO: 7 | 5'-CGGAATTCGCNGTYTTYTCWCC |
| DG149 | SEQ ID NO: 8 | 5'-CGGAATTCGCNGTYTTYTCSCC |
| DG152 | SEQ ID NO: 9 | 5'-CGAGATCTGARGCNGAYGATGT |
| DG153 | SEQ ID NO: 10 | 5'-CGAGATCTGARGCNGAYGACGT |
| DG154 | SEQ ID NO: 11 | 5'-CGAGATCTACNGCNACWGG |
| DG155 | SEQ ID NO: 12 | 5'-CGAGATCTACNGCNACSGG |
| DG156 | SEQ ID NO: 13 | 5'-CGAGATCTCARAAYATHCCWGT |
| DG157 | SEQ ID NO: 14 | 5'-CGAGATCTCARAAYATHCCSGT |
| DG160 | SEQ ID NO: 15 | 5'-CGGAATTCRTCRTGWACCTG |
| DG161 | SEQ ID NO: 16 | 5'-CGGAATTCRTCRTGWACTTG |
| DG162 | SEQ ID NO: 17 | 5'-CGGAATTCRTCRTGSACCTG |
| DG163 | SEQ ID NO: 18 | 5'-CGGAATTCRTCRTGSACTTG |
| DG164 | SEQ ID NO: 19 | 5'-CGAGATCTGGNTAYGTWGAAAC |
| DG165 | SEQ ID NO: 20 | 5'-CGAGATCTGGNTAYGTWGAGAC |
| DG166 | SEQ ID NO: 21 | 5'-CGAGATCTGGNTAYGTSGAAAC |
| DG167 | SEQ ID NO: 22 | 5'-CGAGATCTGGNTAYGTSGAGAC |
| DG168 | SEQ ID NO: 23 | 5'-CGGAATTCGTYTCNACRTAWCC |
| DG169 | SEQ ID NO: 24 | 5'-CGGAATTCGTYTCNACRTASCC |
| DG173 | SEQ ID NO: 25 | 5'-CGGAATTCATYCKYTCSGC |
| DG174 | SEQ ID NO: 26 | 5'-CGGAATTCATRCGYTCSGC |
| DG175 | SEQ ID NO: 27 | 5'-CGGAATTCATYCKYTCWGC |
| DG176 | SEQ ID NO: 28 | 5'-CGGAATTCATRCGYTCWGC |

TABLE 1-continued

Primer Sequences

| | | |
|---|---|---|
| DG181 | SEQ ID NO: 29 | 5'-CGGAATTCNGCNGCNGTSCCYTG |
| DG182 | SEQ ID NO: 30 | 5'-CGGAATTCNGCNGCNGTWCCYTG |
| DG126 | SEQ ID NO: 60 | 5'-CGGAATTCGCCCACATWGGYTC |
| DG127 | SEQ ID NO: 61 | 5'-CGGAATTCGCCCACATSGGYTC |
| DG128 | SEQ ID NO: 62 | 5'-CGAGATCTGGNGAYGAYCCWATG |
| DG129 | SEQ ID NO: 63 | 5'-CGAGATCTGGNGAYGAYCCSATG |
| DG130 | SEQ ID NO: 64 | 5'-CGGAATTCATNGGRTCRTCWCC |
| DG131 | SEQ ID NO: 65 | 5'-CGGAATTCATNGGRTCRTCSCC |
| DG137 | SEQ ID NO: 66 | 5'-CGAGATCTGARGGSGARGA |
| DG140 | SEQ ID NO: 67 | 5'-CGAGATCTGCNCAYATGGAAGC |
| DG141 | SEQ ID NO: 68 | 5'-CGAGATCTGCNCAYATGGAGGC |
| DG150 | SEQ ID NO: 69 | 5'-CGAGATCTGTNTTYGAYGCWAA |
| DG151 | SEQ ID NO: 70 | 5'-CGAGATCTGTNTTYGAYGCSAA |
| DG158 | SEQ ID NO: 71 | 5'-CGGAATTCACNGGDATRTTTTG |
| DG159 | SEQ ID NO: 72 | 5'-CGGAATTCACNGGDATRTTCTG |
| DG183 | SEQ ID NO: 73 | 5'-CAATTCCTAATTGCAAATTCGAAATTGACT-GGCGCGCGGCCCGGGCGGCCCC |
| MK131 | SEQ ID NO: 74 | 5'-CCCGGATCAGGTTCTCGTC |
| MK143 | SEQ ID NO: 75 | 5'-CCGCTGTCCTGGCCCACATG |

A. Protein Sequence Homology

To underscore the power of the degenerate PCR priming method of the invention, information regarding the amino acid and DNA sequence homology between the thermostable DNA polymerases is provided below. Similarity and identity are determined using University of Wisconsin sequence analysis programs (Devereux et al., 1984, *Nuc. Acids Res.* 12(2):387–395).

Amino Acid Homology

| | Taq | | E. Coli | |
|---|---|---|---|---|
| | Similarity | Identity | Similarity | Identity |
| Taq | 100 | 100 | 60.8 | 41 |
| E. coli | 60.8 | 41 | 100 | 100 |

-continued

| | | | | |
|---|---|---|---|---|
| sps17 | 91.4 | 84.1 | 62.5 | 41.9 |
| ZO5 | 93.5 | 86.7 | 59.6 | 40.4 |
| Taf | 62.3 | 41.5 | 62.3 | 41.5 |

DNA Sequence Identity

| | Taq |
|---|---|
| sps17 | 83 |
| ZO5 | 85 |
| Taf | 44.6 |

B. Calculation of Tm

Tm is defined as the temperature at which half of the template is dissociated from the primer. The equation used for the calculation of Tm is derived from the thermodynamic equation:

$$-RT\ln(k_d) = H° - T\Delta S°$$

where R is a constant, T is the temperature (in ° kelvin), $k_d$ is the dissociation constant, H° and S° are the thermodynamic values taken from Breslauer et al., 1986, *Proc. Natl. Acad. Sci. USA* 83:3746–3748. Rearranging the equation:

$$T = H°/(\Delta S° - 2.3R \log_{10}(K_d)).$$

In the presence of primer excess, the $T_m$ is defined as:

$$T_m = H°/(S° - 2.3R \log_{10}[P]),$$

where [P] is the concentration of primer.

The values of H° and S° taken from Breslauer et al. define the $T_m$ in the presence of 1 M NaCl. To correct for the conditions of the PCR buffer (50 mM salt) the following correction is made (taken from Dove et al., *J.M.B.* 5:359 (1966):

$$T_m(\mu_2) - T_m(\mu_1) = 18.51 \log_{10}(\mu_2/\mu_1),$$

where $\mu_1$ and $\mu_2$ are the ionic strengths of the buffer as defined by equation:

$$\mu = \frac{1}{2} \text{ sum } (mZ^2).$$

With the equations above, one can calculate the Tm for the primer pools used in the degenerate priming with respect to either Taq or Taf DNA polymerase gene sequences. The Tm for various pools are shown below; "all" refers to the total primer pool at a concentration of 250 nM, whereas "exact" takes into account the exact concentration of the most completely complementary primer in the pool. The concentration of the most complementary primer is the total concentration divided by the degeneracy of the pool. Lower case letters indicate a base pair mismatch relative to the Taq sequence. The primers were designed to be complementary to the underlined regions; 5' sequences incorporate restriction sites to facilitate cloning of the amplified fragment.

Forward

| | |
|---|---|
| TAQ | CGGGCTAC<u>GAGGCGGACGACGT</u> |
| DG152 | CGaGaTctGARGCNGAyGAtGT |
| DG153 | CGaGaTctGARGCNGAyGACGT |
| CONSENSUS | CGaGaTct<u>GARGCNGAyGAyGT</u> |
| TAF | AAGGCTTT<u>GAAGCTGATGACAT</u> |

Calculated Tm

| | All | Exact |
|---|---|---|
| Taq | 73° C. | 65° C. |
| Taf | 56° C. | 47° C. |

REVERSE

| | |
|---|---|
| TAQ | CTTGACC<u>CCGGGAAGGTTGTC</u> |
| DG144 | CggaAttCCNGGyARRTTaTC |
| DG145 | CggaAttCCNGGyARRTTGTC |
| DG146 | CggaAttCCNGGrAGRTTaTC |
| DG147 | CggaAttCCNGGrAGRTTGTC |
| CONS | CggaAtt<u>CCNGGnARRTTrTC</u> |
| TAF | TTTAACT<u>CCTGGGATATTATC</u> |

Calculated Tm

| | All | Exact |
|---|---|---|
| Taq | 68° C. | 57° C. |
| Taf | 53° C. | 42° C. |

FORWARD

| | |
|---|---|
| TAQ | GGAGGCGGG<u>GGTACGTGGAGAC</u> |
| DG164 | cGAGatctGGNTAyGTwGAaAC |
| DG165 | cGAGatctGGNTAyGTwGAGAC |
| DG166 | cGAGatctGGNTAyGTSGAaAC |
| DG167 | cGAGatctGGNTAyGTSGAGAC |
| CONSENSUS | cGAGatctG<u>GNTAyGTNGARAC</u> |
| TAF | GGAAAAAAG<u>GTTATGTTACAAC</u> |

Calculated Tm

| | All | Exact |
|---|---|---|
| Taq | 62° C. | 52° C. |
| Taf | 47° C. | 38° C. |

REVERSE

| | |
|---|---|
| TAQ | ACCAGC<u>TCGTCGTGGACCTG</u> |
| DG160 | cggAatTCRTCRTGwACCTG |
| DG161 | cggAatTCRTCRTGwACtTG |
| DG162 | cggAatTCRTCRTGSACCTG |
| DG163 | cggAatTCRTCRTGSACtTG |
| CONSENSUS | cggAat<u>TCRTCRTGNACYTG</u> |
| TAF | ACTAAC<u>TCGTCATGAACCTG</u> |

-continued
Calculated Tm

|  | All | Exact |
|---|---|---|
| Taq | 71° C. | 62° C. |
| Taf | 62° C. | 53° C. |

FORWARD

| TAQ | AGACGGCC<u>ACGGCCACGGG</u> |
|---|---|
| DG154 | cGAgatCtACNGCNACwGG |
| DG155 | cGAgatCtACNGCNACsGG |
| CONSENSUS | cGAgatCt<u>ACNGCNACNGG</u> |
| TAF | AAACAGGA<u>ACTTCTACTGG</u> |

Calculated Tm

|  | All | Exact |
|---|---|---|
| Taq | 62° C. | 52° C. |
| Taf | 40° C. | 29° C. |

REVERSE

| TAQ | ATGAGG<u>TCGGCGGCGGTGCCCTG</u> |
|---|---|
| DG181 | cgGAatTCNGCNGCNGTSCCyTG |
| DG182 | cgGAatTCNGCNGCNGTwCCyTG |
| CONSENSUS | cgGAat<u>TCNGCNGCNGTNCCyTG</u> |
| TAF | ATTATA<u>TCAGCTGCTGTTCCTTG</u> |

Calculated Tm

|  | All | Exact |
|---|---|---|
| Taq | 89° C. | 78° C. |
| Taf | 71° C. | 58° C. |

C. General Methodology

Figure 2:
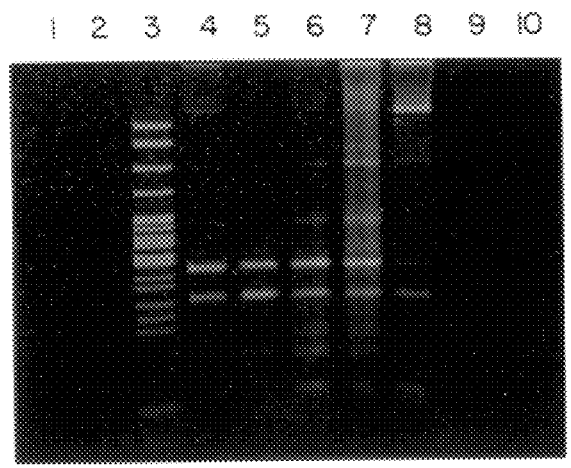
FIG. 2 shows the effect of various PCR profiles on amplification.

Standard 2- and 3-temperature profiles were used for screening degenerate primers on TZ05 and Tsps17 (see U.S. patent application Ser. No. 590,213, filed Sep. 28, 1990, and Ser. No. 590,466, filed Sep. 28, 1990, both incorporated herein by reference). However, it was noted early in the work with Taf that the standard profiles were inadequate. FIG. 1 shows a variety of temperature profiles. FIG. 2 shows the effect of temperature profile on the amplification of a purified DNA fragment. Amplification of Taf chromosomal DNA with the degenerate primer pools DG154-DG155 and DG160-DG164 generated the pattern shown in lane 4 (FIG. 2). The high molecular weight band is the desired fragment (later confirmed by cloning and DNA sequence analysis). The lower molecular weight bands and the general ethidium bromide staining background represent nonspecific amplification which potentially might mask specific amplification products as well as interfere significantly with cloning of the desired band.

Figure 3:
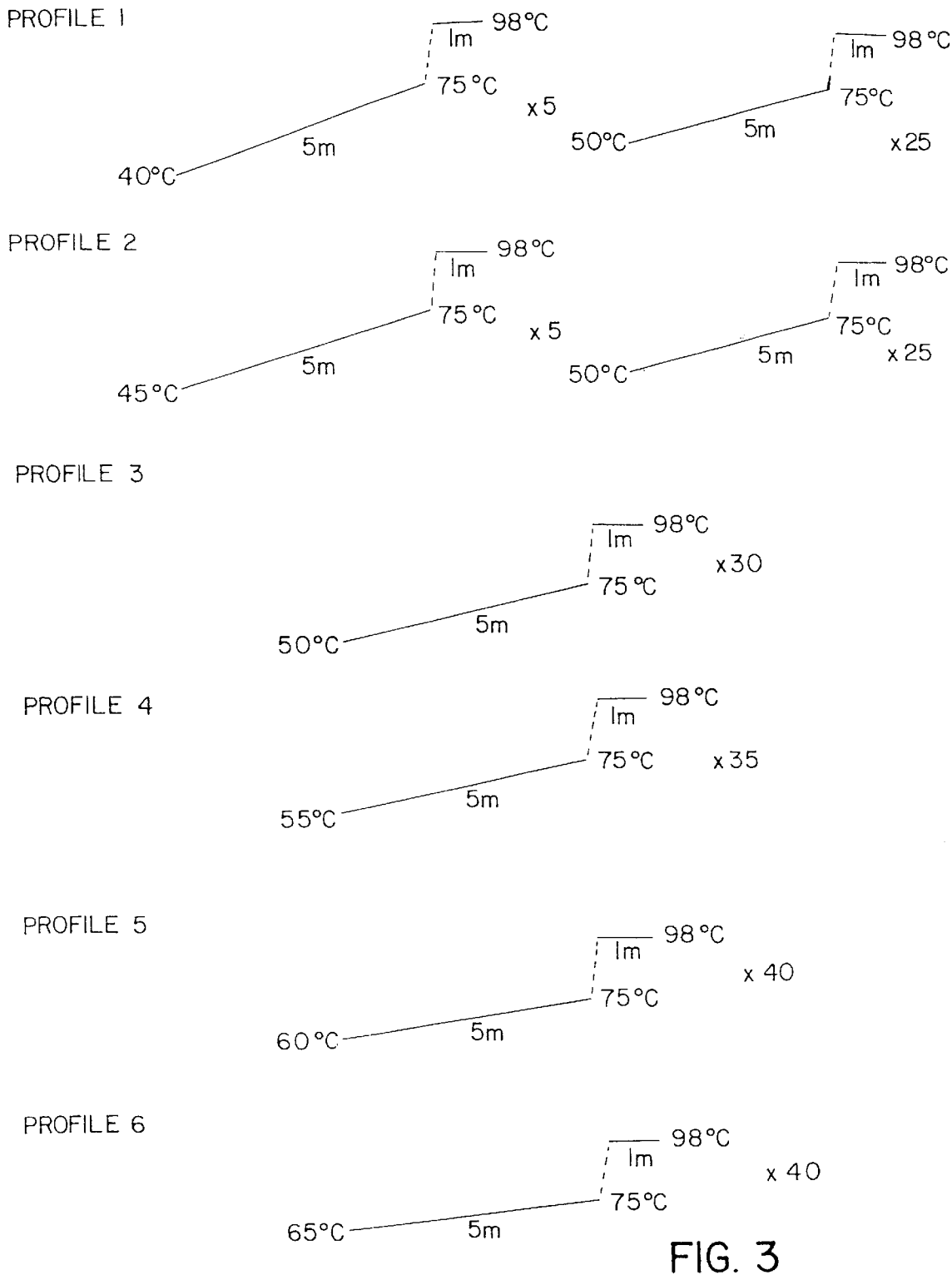
FIG. 3 shows various PCR profiles.

The desired band was purified from an agarose gel and reamplified using temperature profiles 2–5 (FIG. 1 and lanes 5–8 of FIG. 2). Standard 2-temperature profiles (lanes 5 and 6) were inadequate in generating amplification of the purified band. It appeared that amplification of the small amount of contaminating lower molecular weight bands predominated. In contrast, temperature profile 5 (FIG. 3), in which the standard plateau at the lower temperature was replaced by a 5 minute ramp extending between the lower temperature and 75° C., produced the desired band as the predominant product.

Complex temperature profiles were applied to the screening of degenerate primer pools with the Taf chromosomal DNA as shown in FIG. 1. Generally, 5 series of amplifications were performed with many primer pairs. For profiles 1 and 2, an initial 5 cycles of amplification were performed in which a low temperature point was programmed (40° C. and 45° C., respectively) followed by 25 cycles in which the low temperature was programmed at 50° C. In profile 3, 30 cycles were performed with the low temperature programmed at 50° C. Profiles 4, 5 and 6 increased the low temperature point by 5° C. each and increased the cycle number by 5 or 10 cycles. Measurement of in-tube-temperature showed that the temperature in the tube reached 1 to 2° C. above the low temperature setting.

D. Results

Amplification products were obtained from PCR amplification of Taf DNA using the primers listed below. Each amplification yielded products of a molecular weight equal to or greater than that obtained from amplification of Taq DNA using the same degenerate primers. Mismatches between the Taf sequence and the degenerate primers are shown counting from the 3' end of the primer.

DG152-DG153 with DG144-DG147
 −2 (DG152-DG153) and −7 (DG144-DG147)
DG152-DG153 with DG148-DG149
 −2 (DG152-DG153) and −4 (DG148-DG149)
DG154-DG155 with DG160-DG163
 −8 (DG154-DG155)
DG154-DG155 with DG173-DG176
 −8 (DG154-DG155) and −2,−12 (DG173-DG176)
DG154-DG155 with DG181-DG182
 −8 (DG154-DG155)
DG156-DG157 with DG168-DG169
 −1,−2,−8 (DG156-DG157)
DG164-DG167 with DG160-DG163
 −4,−5 (DG164-DG167)

Magnesium concentration is known to affect amplification efficiency. The optimum magnesium concentration depended on both the template and the primer sets used. With DG144-DG147 and DG152-DG153 the optimum magnesium concentration was 3 mM with Taf chromosomal DNA. With the set DG154-DG155 and DG160-DG163 with Taf DNA, the optimum was 2 mM. For the final buffer, 2 mM was standardly used.

EXAMPLE 3

Isolation of DNA Fragments Encoding
*Thermosipho africanus* DNA Polymerase

This example presents a degenerate primer method used to isolate DNA fragments that encode Taf DNA polymerase I. In this method, various sets of forward and reverse primers were used in the polymerase chain reaction. These primers were designed to various conserved motifs comprising the 5'→3' nuclease domain, the template/primer binding domain, the dNTP binding domain, or the single-stranded template DNA binding domain of polymerases of known amino acid sequence (*E. coli*, T7, and Taq). Primer sequences are provided in the Sequence Listing section; Table 1 provides the identification number for each primer.

Pairs of degenerate primers were screened using the sets of six profiles with the modified 5-minute ramp profiles as described in example 2. The amount of magnesium in the amplification was found to effect the amount of PCR product amplified. The magnesium optimum depended both on the primer pairs chosen as well as the template. For screening of the degenerate primer pools on Taf chromosomal DNA, an average magnesium concentration (2 mM) was chosen.

The PCR conditions thus consisted of 10 mM Tris, pH 8.3, 50 mM KCl, 2 mM $MgCl_2$, 200 μM each dNTP, 10 ng chromosomal DNA (at $4.7 \times 10^6$ base pairs per genome, or $5.2 \times 10^{-15}$ g/genome, was equivalent to $3.2 \times 10^{-14}$M genome), 500 nM each oligo primer set, and 2.5–5 units Taq polymerase. A total of 16 pairs of primer pools were used, concentrating on sets to amplify the 5' and 3' end of the coding sequence of the polymerase I gene. Of the 16 sets screened, 7 sets (DG152-DG153 with DG144-DG147, DG152-DG153 with DG148-DG149, DG154-DG155 with DG173-DG176, DG154-DG155 with DG181-DG182, DG154-DG155 with DG160-DG163, DG156-DG157 with DG168-DG169, DG164-DG167 with DG160-DG163) produced discrete bands of a molecular weight equal or greater to that of the Taq product. Four of the PCR products were selected and cloned (DG152-DG153 with DG148-DG149, DG154-DG155 with DG181-DG182, DG154DG155 with DG160-DG163, DG164-DG167 with DG160-DG163). For cloning, the amount of the desired product was enriched. The PCR reaction products were extracted with chloroform to remove the oil, extracted with phenol/chloroform to remove the Taq polymerase, ether extracted to remove residual phenol, and concentrated and desalted over a Biogel P-4 spin column (marketed by Bethesda Research Laboratories). The preparations were electrophoresed on a 3% low melting NuSieve™ GTG agarose gel, and the desired band cut out. The DNA fragment was isolated from the agarose by repeated phenol extractions, ether extractions, and desalting over a Biogel P-4 spin column.

The product was then reamplified with the same primer sets used in the initial generation using protocol 3 (FIG. 3), in which the setting for the initial low-temperature was 50° C. The oil was removed from the reactions by chloroform extraction, the polymerase by phenol extraction, and residual phenol by ether extraction. Following desalting over a biogel P-4 spin column, the preparations were restricted with EcoRI and BglII according to the manufacturer's specifications. These sites were included in the incorporated primer sequences to allow for subsequent cloning, as shown in Table 2. The restriction enzymes were removed by phenol extraction, the samples concentrated and electrophoresed on a 3% low melting NuSieve™ GTG agarose gel. The target band was isolated as described above.

Vector pBSM13+HindIII::BglII was prepared by restricting plasmid with BglII and EcoRI and dephosphorylating with bacterial alkaline phosphatase. Protein was removed by extraction with phenol/chloroform, and the preparation desalted over a Biogel P-4 spin column. Vector pBSM13+ (purchased from Stratagene) was used to make vector pBSM13+HindIII::BglII by digesting vector pBSM13+ with restriction enzyme HindIII, blunting the ends of the digested vector by Klenow treatment, ligating BglII linkers (5'CAGATCTG), transforming host cells, and selecting transformants which contained a plasmid identical to pBSM13+ but for the absence of a HindIII site and the presence of a BglII site.

A sample of the purified fragment and prepared vector were ligated at 10° C. for hours, transformed into DG98, and a sample of the transformed bacteria plated on ampicillin-containing agar plates. Ampicillin-resistant colonies were isolated, and crude plasmid prepared. The correct clones were identified by comparing the size of the insert following restriction of the crude plasmid with EcoRI and BglII with that of the initial PCR product, and comparing the digestion pattern of both the cloned insert with that of the initial PCR product using a variety of restriction endonucleases. Single-stranded DNA was prepared from selected clones and the sequence determined by standard dideoxy sequencing methods. The amino acid sequence deduced from the DNA sequence contained significant homology to known polymerase sequences, suggesting that the PCR products were in fact derived from a Taf polymerase gene.

This strategy resulted in the successful amplification and cloning of various regions of the Taf DNA polymerase gene with the primer pairs shown in Table 2. The primers were designed to be complementary to sequences coding for the amino acid sequences shown; upstream sequences incorporate restriction sites used in the cloning of the amplified product. In Table 2, the amino acid sequence shown below the DNA sequence for the reverse primer is given in the carboxy to amino direction and encoded by the complement of the sequence. The primers shown in Table 2 are characterized as follows.

Synthetic oligodeoxyribonucleotides DG148 and DG149 are two different 32-fold degenerate (each) 22 mer pools designed as "reverse" primers to one of the motifs in the 5' to 3' exonuclease domain (3' most 14 nucleotides) of thermostable DNA polymerases. The primers are designed to complement the (+)-strand DNA sequence that encodes the motif Gly-Glu-Lys-Thr-Ala and which corresponds identically to Taq DNA polymerase amino acids 200 through 204 and to Tth DNA polymerase amino acids 201 through 205. This motif is found in a DNA polymerase gene in all Thermus species. The combined primer pool is 64-fold degenerate and the primers encode an EcoRI recognition sequence at their 5'-ends.

Synthetic oligodeoxyribonucleotides DG152 and DG153 are two different 16-fold degenerate (each) 23 mer pools designed as "forward" primers to one of the motifs in the 5' to 3' exonuclease domain (3' most 14 nucleotides) of thermostable DNA polymerases. This motif is the amino acid sequence Glu-Ala-Asp-Asp-Val and corresponds identically to Taq DNA polymerase amino acids 117 through 121 and to Tth DNA polymerase amino acids 118 through 122. This motif is found in a DNA polymerase gene in all Thermus species. The combined primer pool is 32-fold degenerate and the primers encode a BglII recognition sequence at their 5'-ends.

Synthetic oligodeoxyribonucleotides DG154 and DG155 are two different 32-fold degenerate (each) 19 mer pools designed as "forward" primers to one of the motifs in the primer:template binding domain (3' most 11 nucleotides) of thermostable DNA polymerases. This motif is the tetrapeptide amino acid sequence Thr-Ala-Thr-Gly and corresponds identically to Taq DNA polymerase amino acids 569 through 572, and to Tth and Thermus species Z05 DNA polymerase amino acids 571 through 574. This motif is found in a DNA polymerase gene in all Thermus species. The combined primer pool is 64-fold degenerate and the primers encode a BglII recognition sequence at their 5'-ends.

Synthetic oligodeoxyribonucleotides DG160 through DG163 are four different 8-fold degenerate (each) 20 mer pools designed as "reverse" primers to one of the motifs in the template binding domains (3' most 14 nucleotides) of thermostable DNA polymerases. The primers are designed to complement the (+)-strand DNA sequence that encodes the motif Gln-Val-His-Asp-Glu and which corresponds identically to Taq DNA polymerase amino acids 782 through 786, and to Tth and Thermus species Z05 DNA polymerase amino acids 784 through 788. This motif is found in a DNA polymerase gene in all Thermus species. The combined primer pool is 32-fold degenerate and the primers encode an EcoRI recognition sequence at their 5'-ends.

Synthetic oligodeoxyribonucleotides DG164 through DG167 are four different 16-fold degenerate (each) 22 mer pools designed as "forward" primers to one of the motifs in the template binding domain (3' most 14 nucleotides) of thermostable DNA polymerases. This motif is the pentapeptide amino acid sequence Gly-Tyr-Val-Glu-Thr and corresponds identically to Taq DNA polymerase amino acids 718 through 722, to Tth and Thermus species Z05 DNA polymerase amino acids 720 through 724. This motif is found in a DNA polymerase gene in most Thermus species. The combined primer pool is 64-fold degenerate and the primers encode a BglII recognition sequence at their 5'-ends.

Synthetic oligodeoxyribonucleotides DG181 and DG182 are two different 256-fold degenerate (each) 23 mer pools designed as "reverse" primers to one of the motifs in the template binding domain (3' most 17 nucleotides) of thermostable DNA polymerases. The primers are designed to complement the (+)-strand DNA sequence that encodes the motif Gln-Gly-Thr-Ala-Ala-Asp and which corresponds identically to Taq DNA polymerase amino acids 754 through 759 and to Tth DNA polymerase amino acids 756 through 761. This motif is found in a DNA polymerase gene in all Thermus species. The combined primer pool is 512-fold degenerate and the primers encode an EcoRI recognition sequence at their 5'-ends.

TABLE 2

Degenerate Primer Sets That Produced Correct Regions of Taf Polymerase Gene

| Forward Primer | Sequence | Reverse Primer | Sequence |
| --- | --- | --- | --- |
| DG152-DG153 | GluAlaAspAspVal<br>5'CGAGATCTGARGCNGAYGATGT | DG148-DG149 | 5'CGGAATTCGCNGTYTTYTCWCC<br>AlaThrLysGluGly |
|  | GluAlaAspAspVal<br>5'CGAGATCTGARGCNGAYGACGT |  | 5'CGGAATTCGCNGTYTTYTCSCC<br>AlaThrLysGluGly |
| DG164-DG167 | GlyTyrValGluThr<br>5'CGAGATCTGGNTAYGTWGAAAC | DG160-DG163 | 5'CGGAATTCRTCRTGWACCTG<br>GluAspHisValGln |
|  | GlyTyrValGluThr<br>5'CGAGATCTGGNTAYGTWGAGAC |  | 5'CGGAATTCRTCRTGWACTTG<br>GluAspHisValGln |
|  | GlyTyrValGluThr<br>5'CGAGATCTGGNTAYGTSGAAAC |  | 5'CGGAATTCRTCRTGSACCTG<br>GluAspHisValGln<br>Asp |
|  | GlyTyrValGluThr<br>5'CGAGATCTGGNTAYGTSGAGAC |  | 5'CGGAATTCRTCRTGSACTTG<br>GluAspHisValGln<br>Asp |
| DG154-DG155 | ThrAlaThrGly<br>5'CGAGATCTACNGCNACWGG | DG160-DG163 | 5'CGGAATTCRTCRTGWACCTG<br>GluAspHisValGln<br>Asp |
|  | ThrAlaThrGly<br>5'CGAGATCTACNGCNACSGG |  | 5'CGGAATTCRTCRTGWACTTG<br>GluAspHisValGln<br>Asp |
|  |  |  | 5'CGGAATTCRTCRTGSACCTG<br>GluAspHisValGln<br>Asp |
|  |  |  | 5'CGGAATTCRTCRTGSACTTG<br>GluAspHisValGln<br>Asp |
| DG154-DG155 | ThrAlaThrGly<br>5'CGAGATCTACNGCNACWGG | DG181-DG182 | 5'CGGAATTCNGCNGCNGTSCCYTG<br>AspAlaAlaThrGlyGln<br>Glu |
|  | ThrAlaThrGly<br>5'CGAGATCTACNGCNACSGG |  | 5'CGGAATTCNGCNGCNGTWCCYTG<br>AspAlaAlaThrGlyGln<br>Glu |

The entire coding sequence for Taf polymerase was then identified. Taf chromosomal DNA was digested with BamHI, BglII, ClaI, EcoRI, HindIII, KpnI, PstI, SacI, and SalI according to the manufacturer's specifications and electrophoresed (with radioactively labeled HindIII-digested lambda DNA as a molecular weight marker) on a 0.7% agarose gel. The gel was acid nicked in 0.25 N HCl (30 minutes), and transferred to HybondN+™ nylon membrane (marketed by Amersham) by capillary action in 0.4 N NaOH for 19 hours. The DNA was cross-linked to the membrane by irradiating with 50 mjoules by a Stratalinker™ 1800 (marketed by Stratagene) and treated with prehybridization buffer.

Radioactive probes were generated from the regions encoded between the primer pairs DG160-DG163 and DG164-DG167, and DG144-DG147 to DG152-DG153. Initial PCR product was generated, confirmed by restriction analysis, and purified as described above. Amplification was then repeated using a sample of the purified PCR product as the template, and replacing the dGTP in amplification with 50 $\mu$M $\alpha$-$^{32}$P-dGTP. The oil was removed by chloroform extraction, the polymerase by extraction with phenol/chloroform, the sample concentrated, and unincorporated label removed by desalting over a Biogel P4 spin column. The preparation was electrophoresed on a 3% low melting NuSieve™ GTG agarose gel, and the target radioactively labeled band isolated as described above.

The 3' end of the coding sequence for the polymerase gene was identified by hybridizing the chromosomal blots with 3.6×10$^6$ cpm of probe Taf DG160-DG163 to DG164-DG167 at 50° C. for 17 hours. The blots were washed twice with 2×SSPE, 0.1% SDS at 23° C. for 10 to 25 minutes, then 1×SSPE, 0.1% SDS at 52° C. for 20 minutes and autoradiographed. Discrete bands hybridizing to the probe were identified and their molecular weights determined by comparison to the radioactively labeled lambda markers. Thus, the 3' end of gene was located within the following fragments.

| Enzyme | Molecular weight (bp) of fragment containing 3' end |
| --- | --- |
| BamHI | 6,000 or 21,000 |
| BglII | 2,330 |
| ClaI | 8,100 |
| EcoRI | 4,900 or 6,800 |
| HindIII | 5,350, 3,000 or 1,680 |
| KpnI | 19,500 |
| PstI | 1,410 or 18,000 |
| SacI | >23,000 |
| SalI | >23,000 |

The portion of gene encoding the 5' end of the polymerase sequence was then identified. The 3' probe was removed by boiling the blots in 0.5% SDS, and the membranes hybridized to 3.0×10$^6$ cpm of Taf probe DG152-DG153 to DG148-DG149 at 66° C. for 22 hours. The membranes were washed twice in 2×SSPE, 0.1% SDS at 23° C. for 10 minutes and 1×SSPE, 0.1% SDS at 65° C. for 30 minutes, and autoradiographed. The following fragments were therefore identified as containing sequences that code for the 5' end of the polymerase gene:

| Enzyme | Molecular weight (bp) of fragment containing 5' end |
| --- | --- |
| BamHI | 20,000 |
| BglII | 2,280 |
| ClaI | 7,500 |
| EcoRI | 6,800 |
| HindIII | 2,350 |
| KpnI | 19,500 |
| PstI | 16,000 |
| SacI | 21,000 |
| SalI | >23,000 |

From the two hybridization patterns, it was determined that the gene contains both BglII and HindIII sites. In addition, a 6,800 bp EcoRI fragment contains sequences coding for both the 3' and 5' ends of the polymerase sequence.

The 6,800 bp EcoRI fragment containing the entire gene was then cloned from the chromosome. Taf chromosomal DNA (20 $\mu$g) was digested with EcoRI according to the manufacturer's specifications. The completion of digestion was confirmed by electrophoresis of a sample on a 0.7% agarose gel, acid nicking, transferring to HybondN+™ in 0.4 N NaOH, and probing with radioactively labeled Taf PCR product extending between DG160-DG163 and DG164-DG167. The complete digest was size fractionated by electroelution on a 0.5% SeaKem™ agarose LE gel in TEA and fractions collected. The fractions containing the target EcoRI fragment were identified by electrophresis on a 0.7% agarose gel, which was then acid nicked, transferred to HybondN+™ in 0.4 M NaOH, and hybridized to radioactively labeled Taf PCR product extending between DG160-DG163 and DG164-DG167. The fractions containing the 6,800 bp EcoRI fragment were pooled, concentrated, and desalted over a Biogel P4 spin column.

Three vectors were prepared by digesting pBR322, pUC13, and pBSM13+HindIII::BglII with EcoRI, dephosphorylating with bacterial alkaline phosphatase, extracting with phenol/chloroform and then ether, and desalting over a biogel P-4 spin column. The size fractionated material containing the 6,800 bp-EcoRI fragment was ligated into the vectors, transformed into DG98, and the transformation mixture plated onto ampicillin-containing agar plates.

Following growth at 37° C. for 16 hours, the colonies were lifted onto nitrocellulose filters, lysed with triton lytic buffer, the DNA denatured using 0.5 M NaOH, 1 M NaCl, neutralized with 0.5 M Tris, pH 8.0, 1.0 M NaCl, rinsed with 0.3 M NaCl, 10 mM Tris, pH 7.6, 1 mM EDTA, pH 8.0, and baked at 80° C. for 3 hours. The filters were incubated with prehybridization buffer at 65° C. for 1 hour and hybridized with 4.4×10$^5$ CPM of radioactively labeled Taf PCR product extending between DG160-DG163 and DG164-DG167 for 15 hours at 50° C. The filters were washed in 5×SSC, 0.1% SDS at 23° C. for 16 minutes, 2×SSC, 0.1% SDS at 23° C. for 30 minutes, and autoradiographed.

Probe positive colonies were inoculated into broth containing ampicillin and methicillin and grown at 37° C. The correct clones were identified by isolating plasmid DNA followed by restriction enzyme analysis. Clones containing a 6.8 kb insert were identified by restriction with EcoRI. The correct clones were further identified by restriction analysis with HindIII, HindIII and EcoRI or BglII, because it was determined in the chromosomal mapping that the polymerase gene contained both HindIII and BglII sites.

For further confirmation, the restriction digests of the suggested clones were electrophoresed on a 0.7% agarose gel, and the DNA bands transferred to HybondN+™ and probed with radioactively labeled Taf PCR product extending between DG160-DG163 and DG164-DG167, and subsequently with radioactively labeled Taf PCR product extending between DG144-DG147 and DG152-DG153 as previously described. Several clones were confirmed as correct (52-1, 52-2, 52-3, 52-6, 52-7, and 52-9).

To facilitate sequencing and subsequent manipulation of the polymerase gene for the construction of expression vectors, a smaller 3,000 bp EcoRV fragment was subcloned from the larger 6,800 bp EcoRI fragment. Clone 52-1, containing the 6,800 EcoRI fragment was digested with EcoRV, according to the manufacturer's specifications, concentrated, desalted over a biogel P-4 spin column, and electrophoresed on a 1% low melting NuSieve™ GTG agarose gel. The target band was then purified as previously described.

For the vector, pBSM13+HindIII::BglII was restricted with SmaI and dephosphorylated by bacterial alkaline phosphatase. The protein was removed by phenol/chloroform extraction, and the preparation desalted over a Biogel P-4 spin column. A sample of the vector and purified fragment was ligated with T4 DNA ligase and T4 RNA ligase at 23° C. for 7 hours, transformed into DG98 and the transformation fixture plated on ampicillin-containing agar plates. Ampicillin-resistant colonies were selected and grown in liquid broth, and crude plasmid preparations isolated.

The size of the insert was determined by restriction with EcoRI and BamHI, which cut the vector on both sides of the SmaI site that contained the insert. The identity of the insert was further confirmed by restriction with BglII, a site previously determined to be within the gene from the mapping of the chromosome (described above), EcoRI with ClaI, and EcoRI with SpeI. Clones were identified which contained the polymerase gene in both orientations. The orientation that placed the coding sequence in position for expression from the lac promoter was designated pBSM:TafEcoRV.

EXAMPLE 4

Construction of *Thermosipho africanus* DNA Polymerase Expression Vectors

The entire Taf DNA polymerase coding sequence can be isolated from Taf genomic DNA on an approximately 3 kb EcoRV fragment. This EcoRV fragment was isolated and cloned into the Stratagene™ vector pBSM13+, which had first been digested with restriction enzyme SmaI. The resulting vector was designated pBSM:TafEcoRV, and the orientation of the Taf gene EcoRV DNA fragment is such that the lac promoter, ribosome-binding site (RBS), and ATG start codon for the coding sequence of beta-galactosidase from the pBSM13+ vector are positioned for expression of the Taf DNA polymerase coding sequence. The ATG start codon of the Taf DNA polymerase coding sequence is about 20 bp from the EcoRV restriction enzyme recognition site, which is, in turn, about 84 bp from the ATG of the beta-galactosidase coding sequence.

Oligonucleotide site-directed mutagenesis was then used to alter the carboxy terminus encoding region of the Taf DNA polymerase coding sequence in plasmid pBSM:TafEcoRV. Single-stranded plasmid DNA was prepared by infecting a log phase culture of DG98 harboring the plasmid with helper phage R408. Single-stranded DNA was recovered and purified via electroelution. Gapped-duplex DNA was formed between the single-stranded pBSM:TafEcoRV and the large PvuII fragment of vector pBSM13+, and then the gapped duplex was annealed with mutagenic oligomer, either DG233 or DG234. Extension and ligation of the reactions containing mutagenic oligomers annealed to gapped duplex was performed, and the mixtures were transformed into DG101. Transformed colonies on nitrocellulose filters were screened by hybridization with γ-$^{32}$P-labeled oligomer DG235. Mini-screen DNA prepared from positive single colonies was analyzed by restriction analysis to confirm the presence of a new BamHI site, loss of a BglII site, and the appropriate PvuII pattern. DNA sequence analysis confirmed the mutagenesis.

The sequences of the mutagenic and probe oligomers are shown below.

```
DG233  SEQ ID NO: 31  5'-GCGAATTCGAGCTCGGTACC-
                        GGATCCTCATTCCCACTCTTTTCC

DG234  SEQ ID NO: 32  5'-CCTTTACCCCAGGATCCTCAT-
                        TCCCACTCTTTTCC

DG235  SEQ ID NO: 33  5'-GATCCTCATTCCCACTC
```

Mutagenesis with DG233 changed the TAA stop codon to TGA, created a BamHI restriction site immediately following the new TGA stop codon, and deleted Taf and vector sequences to the KpnI site in the polylinker of the vector, a deletion of 213 bp. One of the correct mutants from the DG233 mutagenesis was designated pTaf01.

Mutagenesis with DG234 changed the TAA stop codon to TGA and created a new BamHI site directly downstream of the TGA stop, but deleted no Taf or vector sequences downstream of the BamHI site. One of the correct mutants from the DG234 mutagenesis was designated pBSM:TafRV3' and can be used to construct expression vectors as illustrated with pTaf01, below.

Oligonucleotide site-directed mutagenesis was used to alter the 5'-end of the Taf DNA polymerase gene in pTaf01. Mutagenesis was as described above, using mutagenic oligonucleotide DG248 to insert an NcoI restriction site at the ATG start of the Taf DNA polymerase coding sequence and to delete vector and Taf sequences to make the lacZ ATG start codon the start codon for the Taf DNA polymerase coding sequence. Transformed colonies on nitrocellulose filters were screened by hybridization with γ-$^{32}$P-labeled oligonucleotide DG237. The sequences of the mutagenic and probe oligomers are shown below.

```
DG248  SEQ ID NO: 34 5'-CAAATAGAAACATCTTTCCC-
                       ATGGCTGTTTCCTGTGTGAAATTG

DG237  SEQ ID NO: 35 5'-GAAACAGCCATGGGAAAG
```

Mini-screen DNA prepared from positive colonies was subjected to restriction analysis to confirm the presence of the new NcoI site and the deletion. DNA sequence analysis was also performed to ensure that the correct sequence was obtained. The correct plasmid was designated pTaf02. IPTG-induced cultures harboring pTaf02 expressed heat-stable polymerase activity at 24 units per mg crude extract protein (where a pBSM13+ control culture was 0.04 units per mg crude extract protein, and the pBSM:TafEcoRV culture was 6.5 units per mg crude extract protein).

The 2.7 kb NcoI-BamHI DNA fragment comprising the Taf DNA polymerase coding sequence in pTaf02 was cloned into four P$_L$ expression plasmids, pDG182-pDG185, which had been digested with NcoI and BamHI. Plasmids pDG182 and pDG184 are derivatives of pDG160, and pDG183 and pDG185 are derivatives of pDG161. The construction of plasmids pDG160 and pDG161 is described in Example 6 of Ser. No. 455,967, filed Dec. 22, 1989, the entire disclosure of which is incorporated herein by reference. The preferred host for such expression vectors is *E. coli* K12 strain DG116, and culture of the host cells and induction of expression is carried out as described in Example 7 of Ser. No. 455,967.

To construct expression vectors pDG182-pDG185, plasmids pDG160 and pDG161 were digested with restriction enzymes MroI and KpnI, and the smaller of the resulting two fragments was replaced with a duplex adaptor linker, either FL42/FL43 or FL44/FL45, and the vector recircularized by ligation. The sequence of the duplex adaptor linkers FL42 (SEQ. ID NO: 36); FL43 (SEQ. ID NO: 37); FL44 (SEQ. ID NO: 38); and FL45 (SEQ. ID NO: 39) are shown below.

FL42/FL43

5'-CCGGAAGAAGGAGAAAATACCATGGGCCC-GGTAC-3+
3'-TTCTTTCTCTTTTATGGTACCCGGGC-5'

FL44/FL45

5'-CCGGAGGAGAAAATCCATGGGCCCGGTAC-3'
3'-TCCTCTTTTAGGTACCCGGGC-5'

The following table describes the properties of plasmids pDG182-pDG185.

| Vector | Amp$^R$ or Tet$^R$ | RBS | Site at ATG | Oligonucleotide Duplex Cloned into pDG160 or pDG161 |
|---|---|---|---|---|
| pDG182 | Amp | T7 | NcoI | FL42/FL53-pDG160 |
| pDG184 | Amp | N | NcoI | FL42/FL45-pDG160 |
| pDG183 | Tet | T7 | NcoI | FL42/FL43-pDG161 |
| pDG185 | Tet | N | NcoI | FL44/FL45-pDG161 |

In addition to the features tabulated above, the pDG182-pDG185 vectors also contain the δ-toxin positive retroregulator from *Bacillus thuringiensis* and point mutations in the RNA II gene which render the plasmids temperature sensitive for copy number.

Derivatives of pDG182-pDG185 containing the 2.7 kb NcoI to BamHI fragment are pTaf03 (from pDG182), pTaf04 (from pDG183), pTaf05 (from pDG184), and pTaf06 (from pDG185). These plasmids produce Taf DNA polymerase activity when expression is induced.

EXAMPLE 5

PCR with Taf DNA Polymerase

About 1.25 units of the Taf DNA polymerase purified in Example 1 is used to amplify sequences from Tth genomic DNA. The reaction volume is 50 µl, and the reaction mixture contains 50 pmol of primer DG73, $10^5$ to $10^6$ copies of the Tth genome (~2×$10^5$ copies of genome/ng DNA), 50 pmol of primer DG74, 200 µM of each dNTP, 2 mM MgCl$_2$, 10 mM Tris-HCl, pH 8.3, 50 mM KCl, and 100 µg/ml gelatin (optionally, gelatin may be omitted).

The reaction is carried out on a Perkin-Elmer Cetus Instruments DNA Thermal Cycler. Twenty to thirty cycles of 96° C. for 15 seconds; 50° C. for 30 seconds, and 75° C. for 30 seconds are carried out. At 20 cycles, the amplification product (160 bp in size) can be faintly seen on an ethidium bromide stained gel, and at 30 cycles, the product is readily visible (under UV light) on the eithidium bromide stained gel.

The PCR may yield fewer non-specific products if fewer units of Taf DNA polymerase are used (i.e., 0.31 units/50 µl reaction). Furthermore, the addition of a non-ionic deterent, such as laureth-12, to the reaction mixture to a final concentration of 1% can improve the yield of PCR product.

Primers DG73 and DG74 are shown below:

DG73 SEQ ID NO: 40
5'-TACGTTCCCGGGCCTTGTAC

DG74 SEQ ID NO: 41
5'-AGGAGGTGATCCAACCGCA

EXAMPLE 6

Expression of modified Taf polymerase

In an effort to increase the expression levels, site specific mutagenesis was performed to (1) remove the predicted hairpin structure from codons 2 to 6 of the coding sequence; and (2) change codons 2, 5, 6, 7, 9, and 11 to codons used more commonly in *E. coli* than the codons present in the native sequence. Mutagenic primers, FR404 or FR405, each containing a modified sequence were synthesized and phosphorylated. The modified codon 9 and codon 10 form a KpnI site. Single-stranded pTaf02 was prepared by coinfecting a log phase culture of DG101 containing the plasmid with the helper phage R408, commercially available from Stratagene. A "gapped duplex" of single stranded pTaf02 and the large fragment from the PvuII digestion of pBSM13+ was created by mixing the two plasmids, heating to boiling for 2 minutes, and cooling to 65° C. for 5 minutes. Mutagenic primer FR404 or FR405 was then annealed with the "gapped duplex" by mixing, heating to 80° C. for 2 minutes, and then cooling slowly to room temperature. The remaining gaps were filled by extension with Klenow and the fragments ligated with T4 DNA ligase, both reactions taking place in 200 µM of each dNTP and 40 µM ATP in standard salts at 37° C. for 30 minutes.

The resulting circular fragment was transformed into DG101 host cells by plate transformations on nitrocellulose filters. Duplicate filters were made and the presence of the correct plasmid was detected by probing with a $\gamma^{32}$P-phosphorylated probe; FR401 was used to screen for the product of mutagenesis with FR404 and FR399 was used to screen for the product of mutagenesis with FR405. Miniscreen DNA prepared from positive colonies was subjected to restriction analysis to confirm the presence of the NcoI site from pTaf02 and the introduced KpnI site, after which the DNA sequence was confirmed. Two expression vectors were produced by the above protocol; the vector created using FR404 was designated pTaf07 and the vector created using FR405 was designated pTaf08.

The oligonucleotide sequences used in this example are listed below.

| Oligo | SEQ ID NO: | Sequence |
|---|---|---|
| FR399 | SEQ ID NO: 42 | 5'-TAAGATGTTCTTGTTC |
| FR401 | SEQ ID NO: 43 | 5'-TAAGATGTTCCTGTTC |
| FR404 | SEQ ID NO: 44 | 5'-ATACTAAACCGGTACCAT-CGAACAGGAACATCTTACCCATGGC |
| FR405 | SEQ ID NO: 45 | 5'-ATACTAAACCGGTACCA-TCGAACAAGAACATCTTACCCATGGC |

EXAMPLE 7

Expression of Truncated Taf Polymerase

Mutein forms of the Taf polymerase lacking 5'→3' exonuclease activity were constructed by introducing deletions in the 5' end of the gene. Both 279 and 417 base pair deletions were created using the following protocol; an expression plasmid was digested with restriction enzymes to excise the desired fragment, the fragment ends were repaired with Klenow and all four dNTP's, to produce blunt ends, and the products were ligated to produce a new circular plasmid with the desired deletion. To express a 93 kilodalton, 5'→3' exonuclease-deficient form of Taf polymerase, a 279 bp deletion comprising amino acids 2–93 was generated. To express an 88 kilodalton, 5'→3' exonuclease-deficient form of Taf polymerase, 417 bp deletion comprising amino acids 2–139 was generated.

To create a plasmid with codons 2–93 deleted, pTaf03 was digested with NcoI and NdeI and the ends were repaired by Klenow treatment. The digested and repaired plasmid was diluted to 5 μg/ml and ligated under blunt end conditions. The dilute plasmid concentration favors intramolecular ligations. The ligated plasmid was transformed into DG116. Mini-screen DNA preparations were subjected to restriction analysis and correct plasmids were confirmed by DNA sequence analysis. The resulting expression vector created by deleting a segment from pTaf03 was designated pTaf09. A similar vector created from pTaf05 was designated pTaf10.

Expression vectors also were created with codons 2–139 deleted. The same protocol was used with the exception that the initial restriction digestion was performed with NcoI and BglII. The expression vector created from pTaf03 was designated pTaf11 and the expression vector created from pTaf05 was designated pTaf12.

EXAMPLE 8

Expression Vectors With T7 Promoters

Expression efficiency can be altered by changing the promoter and/or ribosomal binding site (RBS) in an expression vector. The T7 gene 10 promoter and RBS were used to control the expression of Taf DNA polymerase in expression vector pTaf13, and the T7 gene 10 promoter and the gene N RBS were used to control the expression of Taf DNA polymerase in expression vector pTaf14. The construction of these vectors took advantage of unique restriction sites present in pTaf05: an AflII site upstream of the promoter, an NcoI site downstream of the RBS, and a BspEI site between the promoter and the RBS. The existing promoter was excised from pTaf05 and replaced with a synthetic T7 gene 10 promoter using techniques similar to those described in the previous examples.

The synthetic insert was created from two overlapping synthetic oligonucleotides. To create pTaf13, equal portions of FR414 and FR416 were mixed, heated to boiling, and cooled slowly to room temperature. The hybridized oligonucleotides were extended with Klenow to create a full-length double-stranded insert. The extended fragment was then digested with AflII and NcoI, leaving the appropriate sticky ends. The insert was cloned into plasmid pTaf05 digested with AflII and NcoI. DG116 host cells were transformed with the resulting plasmid and transformants screened for the desired plasmid.

The same procedure was used in the creation of pTaf14, except that FR414 and FR418 were used, and the extended fragment was digested with AflII and BspEI. This DNA fragment was substituted for the $P_L$ promoter in plasmid pTaf05 that had been digested with AflII and BspEI.

Plasmids pTaf13 and pTaf14 are used to transform E. coli host cells that have been modified to contain an inducible T7 RNA polymerase gene. However, because T7 RNA polymerase may not recognize the δ-toxin retroregulator terminator sequence present in the plasmid vector, it may be desirable to clone the T7 gene 10 terminator sequence into pTaf13 or pTaf14.

The T7 gene 10 terminator sequence was first cloned into a small, high copy number E. coli cloning vector, pUC19, available as ATCC 37254 (see Yanisch-Perron, et al., 1985, Gene 33:103–119). Synthetic oligonucleotides, HW73 and HW75, were annealed to provide the T7 gene 10 terminator sequence flanked by HindIII sticky ends. The pUC19 plasmid was digested with HindIII and ligated with the HW73/HW75 duplex. The resulting plasmid, designated pTW66, was transformed into DG101 and screened for orientation by restriction enzyme digestion and DNA sequence analyses.

A second vector was created from pUC19 by inserting the T7 promoter sequence. Synthetic oligonucleotides, HW71 and HW72, were annealed to provide the T7 promoter sequence flanked by BamHI sticky ends. The pUC19 plasmid was digested with BamHI and ligated with the HW71/HW72 duplex. The resulting plasmid, designated pTW64, was transformed into DG101 and screened for orientation by restriction analyses and sequence analysis.

A 95 bp fragment containing the T7 promoter was isolated from pTW64 by digestion with EcoRI and HindIII and separation of the restriction fragments by gel electrophoresis. The pTW66 plasmid was digested with EcoRI and HindIII and ligated with the purified fragment from the digestion of pTW64. The resulting vector, designated pTW67, contains both the T7 promoter sequence and gene 10 terminator sequence.

The T7 gene 10 terminator sequence is excised from the pTW67 vector by digestion with XhoI and SalI. The vector is also cut with PvuII to reduce background. The pTaf13 vector is cut with SalI which cleaves at a unique site just downstream of the existing terminator. Digestions with XhoI and SalI leave the same sticky end for ligation. The fragment containing the T7 gene 10 terminate sequence is ligated with the cleaved pTaf13. The resulting plasmid, designated pTaf16, is transformed into MM294 and screened for orientation.

The expression plasmid pTaf16, which contains the T7 gene 10 promoter, RBS, and the T7 gene 10 terminator, is transformed into an E. coli host cell modified to contain an inducible T7 RNA polymerase gene.

The oligonucleotides used in the construction of these vectors are listed below.

```
FR414  SEQ ID NO: 46   5'-TCAGCTTAAGACTTCGAAATTAATA-
                       CGACTCACTATAGGGAGACCACAA-
                       CGGTTTCCCTC

FR416  SEQ ID NO: 47   5'-TCGACCATGGGTATATCTCCTT-
                       CTTAAAGTTAAACAAAATTATTTC-
                       TAGAGGGAAACCGTTG

FR418  SEQ ID NO: 48   5'-TCAGTCCGGATAAACAAAA-
                       TTATTTCTAGAGGGAAACCGTTG

HW71   SEQ ID NO: 49   5'-GATCACTTCGAAATTAA-
                       TACGACTCACTATAGGGAGACCG

HW72   SEQ ID NO: 50   5'-GATCCGGTCTCCCTATAGTGAG-
                       TCGTATTAATTTCGAAGT

HW73   SEQ ID NO: 51   5'-AGCTTTAAAGATCTAATAACTA-
                       GCATAACCCCTTGGGGCCTCTAAA-
                       CGGGTCTTGAGGGGTTTTTTGCTGA-
                       CTCGAG

HW75   SEQ ID NO: 52   5'-AGCTCTCGAGTCAGCAAAAAACCCC-
                       TCAAGACCCGTTTAGAGGCCCCAA-
                       GGGGTTATGCTAGTTATTAGATCTTTAA
```

EXAMPLE 9

Translational Coupling

To effect the translation of the Taf polymerase gene, translationally coupled derivatives of Taf expression vectors were constructed. An expression vector was constructed with a secondary translation initiation signal and short coding sequence just upstream of the Taf gene coding sequence such that the stop codon for the short coding sequence is coupled, i.e., overlaps, with the ATG start codon for the Taf gene coding sequence. Translation of the short coding sequence brings the ribosome into close proximity with the Taf gene translation initiation site, thereby enhancing translation of the Taf gene.

Translationally coupled Taf expression vectors were constructed with the translation initiation signal and first ten codons of the T7 bacteriophage major capsid protein (gene 10) fused in-frame to the last six codons of the *E. coli* TrpE gene placed upstream of the Taf coding region. The TGA (stop) codon for TrpE is "coupled" with the ATG (start) codon for the Taf gene, forming the sequence TGATG as it is coupled with the ATG (start) codon for TrpD on the *E. coli* chromosome. A one base frame-shift is required between translation of the short coding sequence and translation of the Taf coding sequence.

In the example below, a fragment containing the T7 gene 10-*E. coli* TrpE/TrpD fusion product (the last 6 codons and TGA stop codon from TrpE along with the overlapping ATG start codon from TrpD) was obtained from a pre-existing plasmid. One of ordinary skill will recognize that the T7 gene 10-*E. coli* TrpE/TrpD fusion product used in the construction of the translationally coupled expression vectors can be constructed from synthetic oligonucleotides. The sequence for the inserted fragment is listed below.

The T7 gene 10-*E. coli* TrpE/TrpD fusion product was amplified using plasmid pSYC1868 and primers FL48 and FL50. FL52 and FL54 were used to amplify the 5' end of the Taf Pol I gene in pTaf02 from the ATG start codon to the BglII site downstream of the ATG start codon. The primers FL50 and FL52 were designed to be partially complementary. Consequently, the extension product of FL48 can hybridize to the extension product of FL54. The two amplification products were mixed, heated to 95° C. and slowly cooled to room temperature to anneal. Hybrids formed between the extension products of FL48 and FL54 were extended with Taq polymerase to form a full length double-stranded molecule.

The extended insert was amplified with primers FL48 and FL54 and then digested with MroI and BglII. Plasmid pTaf03 was digested with MroI and BglII, then treated with calf intestine alkaline phosphatase to prevent re-ligation. The digested pTaf03 was ligated with the insert. DG116 host cells were transformed with the resulting construct and transformants screened for the desired plasmid DNA. The resulting vector was designated pTaf15.

The sequences of the oligonucleotide primers and the T7 gene 10-*E. coli* TrpE/TrpD fusion product (gene 10 insert) are listed below.

| Primers | SEQ ID NO: | Sequence |
|---|---|---|
| FL48 | SEQ ID NO: 53 | 5'-TCCGGACTTTAAGAAGGAGATATAC |
| FL50 | SEQ ID NO: 54 | 5'-AACATCTTACCCATCAGAAAGTCTCCTGTGC |
| FL52 | SEQ ID NO: 55 | 5'-AGACTTTCTGATGGGTAAGATGTTC |
| FL54 | SEQ ID NO: 56 | 5'-AACAAGTTGTAAAAGATCTTTATCTCCAG |
| Gene 10 insert | SEQ ID NO: 57 | 5'-CTTTAAGAAGGAGATATACATATGGCTAG-CATGACTGGTGGACAGCAAATGCATGCACA-GGAGACTTTCTGATG |

EXAMPLE 10

Arg U tRNA Expression

The pattern of codon usage differs between *Thermosipho africanus* and *E. coli*. In the Taf coding sequence, arginine is most frequently coded for by the AGA codon, whereas this codon is used in low frequency in *E. coli* host cells. The corresponding Arg U tRNA appears in low concentrations in *E. coli*. The low concentration in the host cell of Arg tRNA using the AGA codon may limit the translation efficiency of the Taf polymerase gene. The efficiency of translation of the Taf coding sequence within an *E. coli* host may be improved by increasing the concentration of this tRNA species by cloning multiple copies of the tRNA gene into the host cell using a second expression vector that contains the gene for the "Arg U" tRNA.

The Arg U tRNA gene was PCR amplified from *E. coli* genomic DNA using the primers DG284 and DG285. The amplification product was digested with SalI and BamHI. The ColEI compatible vector pACYC184, commercially available from New England Biolabs, was digested with SalI and BamHI, and the Arg U gene fragment was subsequently ligated with the digested vector. DG101 cells were transformed, and the ligated vector was designated pARG01. Finally, DG116 host cells were co-transformed with pARG01 and pTaf03.

The oligonucleotide primers used in this Example are listed below.

| Primers | SEQ ID NO: | Sequence |
|---------|-----------|----------|
| DG284 | SEQ ID NO: 58 | 5'-CGGGGATCCAAAAGCCATTGACTCAGCAAGG |
| DG285 | SEQ ID NO: 59 | 5'-GGGGGTCGACGCATGCGAGGAAAATAGACG |

EXAMPLE 11

Purification of Recombinant Taf Polymerase

Recombinant Taf DNA Polymerase can be purified from the expression host/vector combinations described, for example, *E. coli* strain DG116 containing one of the expression vectors described in Example 4, above, using the following protocol.

The seed flask for a 10 L fermentation contains tryptone (20 g/l), yeast extract (10 g/l), NaCl (10 g/l), glucose (10 g/l), ampicillin (50 mg/l), and thiamine (10 mg/l). The seed flask is inoculated with a colony from an agar plate (a frozen glycerol culture can be used). The seed flask is grown at 30° C. to between 0.5 to 2.0 O.D. ($A_{680}$). The volume of seed culture inoculated into the fermentor is calculated such that the bacterial concentration is 0.5 mg dry weight/liter. The 10 liter growth medium contains 25 mM $KH_2PO_4$, 10 mM $(NH_4)_2SO_4$, 4 mM sodium citrate, 0.4 mM $FeCl_3$, 0.04 mM $ZnCl_2$, 0.03 mM $CoCl_2$, 0.03 mM $CuCl_2$, and 0.03 mM $H_3BO_3$. The following sterile components are added: 4 mM $MgSO_4$, 20 g/l glucose, 20 mg/l thiamine, and 50 mg/l ampicillin. The pH is adjusted to 6.8 with NaOH and controlled during the fermentation by added $NH_4OH$. Glucose is continually added by coupling to $NH_4OH$ addition. Foaming is controlled by the addition of propylene glycol as necessary, as an antifoaming agent. Dissolved oxygen concentration is maintained at 40%.

The fermentor is inoculated as described above, and the culture is grown at 30° C. to a cell density of 0.5 to $1.0 \times 10^{10}$ cells/ml (optical density [$A_{680}$] of 15). The growth temperature is shifted to between 37° C. and 41° C. to induce the synthesis of Taf DNA polymerase. The temperature shift increases the copy number of the expression plasmid and simultaneously derepresses the lambda $P_L$ promoter controlling transcription of the modified Taf DNA polymerase gene through inactivation of the temperature-sensitive cI repressor encoded by the defective prophage lysogen in the host.

The cells are grown for 6 hours to an optical density of 37 ($A_{680}$) and harvested by centrifugation. The cell mass (ca. 95 g/l) is resuspended in an equivalent volume of buffer containing 50 mM Tris-Cl, pH 7.6, 20 mM EDTA and 20% (w/v) glycerol. The suspension is slowly dripped into liquid nitrogen to freeze the suspension as "beads" or small pellets. The frozen cells are stored at −70° C.

To 200 g of frozen beads (containing 100 g wet weight cell) is added 100 ml of 1× TE (50 mM Tris-Cl, pH 7.5, 10 mM EDTA) and Dithiothreitol (DTT) to 0.3 mM, phenylmethanesulfonyl flouride (PMSF) to 2.4 mM, leupeptin to 1 µg/ml and L-1-Chloro-3-[4-tosylamido]-7-amino-2-heptanone-HCl (TLCK) (the latter three are protease inhibitors) to 0.2 mM. The sample is thawed on ice and uniformly resuspended in a blender at low speed. The cell suspension is lysed in an Aminco french pressure cell at 20,000 psi. To reduce viscosity, the lysed cell sample is sonicated 4 times for 3 min. each at 50% duty cycle and 70% output. The sonicate is adjusted to 550 ml with 1× TE containing 1 mM DTT, 2.4 mM PMSF, 1 µg/ml leupeptin and 0.2 mM TLCK (Fraction I). After addition of ammonium sulfate to 0.3 M, the crude lysate is rapidly brought to 75° C. in a boiling water bath and transferred to a 75° C. water bath for 15 min. to denature and inactivate *E. coli* host proteins. The heat-treated sample is chilled rapidly to 0° C. and incubated on ice for 20 min. Precipitated proteins and cell membranes are removed by centrifugation at 20,000×G for 30 min. at 5° C. and the supernatant (Fraction II) saved.

The heat-treated supernatant (Fraction II) is treated with polyethyleneimine (PEI) to remove most of the DNA and RNA. Polymin P (34.96 ml of 10% [w/v], pH 7.5) is slowly added to 437 ml of Fraction II at 0° C. while stirring rapidly. After 30 min. at 0° C., the sample is centrifuged at 20,000×G for 30 min. The supernatant (Fraction III) is applied at 80 ml/hr to a 100 ml phenylsepharose column (3.2×12.5 cm) that has been equilibrated in 50 mM Tris-Cl, pH 7.5, 0.3 M ammonium sulfate, 10 mM EDTA, and 1 mM DTT. The column is washed with about 200 ml of the same buffer ($A_{280}$ to baseline) and then with 150 ml of 50 mM Tris-Cl, pH 7.5, 100 mM KCl, 10 mM EDTA and 1 mM DTT. The Taf DNA polymerase is then eluted from the column with buffer containing 50 mM Tris-Cl, pH 7.5, 2 M urea, 20% (w/v) ethylene glycol, 10 mM EDTA, and 1 mM DTT, and fractions containing DNA polymerase activity are pooled (Fraction IV).

Fraction IV is adjusted to a conductivity equivalent to 50 mM KCl in 50 mM Tris-Cl, pH 7.5, 1 mM EDTA, and 1 mM DTT. The sample is applied (at 9 ml/hr) to a 15 ml heparin-sepharose column that has been equilibrated in the same buffer. The column is washed with the same buffer at ca. 14 ml/hr (3.5 column volumes) and eluted with a 150 ml 0.05 to 0.75 M KCl gradient in the same buffer. Fractions containing the Taf DNA polymerase are pooled, concentrated, and diafiltered against 2.5× storage buffer (50 mM Tris-Cl, pH 8.0, 250 mM KCl, 0.25 mM EDTA, 2.5 mM DTT, and 0.5% Tween 20), subsequently mixed with 1.5 volumes of sterile 80% (w/v) glycerol, and stored at −20° C.

Optionally, the heparin sepharose-eluted DNA polymerase or the phenyl sepharose-eluted DNA polymerase can be dialyzed or adjusted to a conductivity equivalent to 50 mM KCl in 50 mM Tris-Cl, pH 7.5, 1 mM DTT, 1 mM EDTA, and 0.2% Tween 20 and subjected to nucleotide binding protein affinity chromatography. The polymerase containing extract is applied (1 mg protein/ml resin) to an affigel blue column that has been equilibrated in the same buffer. The column is washed with three to five column volumes of the same buffer and eluted with a 10 column volume KCl gradient (0.05 to 0.8 M) in the same buffer. Fractions containing DNA polymerase activity are pooled, concentrated, diafiltered, and stored as above.

Optionally, the pooled fractions can be subjected to cation exchange chromatography. The fractions are applied to a 2 ml CM-Tris-Acryl M (LKB) column equilibrated with a buffer consisting of 25 mM sodium acetate, 20 mM NaCl, 0.1 mM EDTA, 1 mM DTT, and 0.2% Tween 20 at pH 5.0. The column is washed with 4–5 column volumes of the same buffer and the enzyme eluted with a linear gradient form 20 to 400 mM NaCl in sodium acetate buffer. Active fractions are pooled, concentrated, diafiltered, and stored as above.

Deposits

The following deposit was made on the date given:

| Strain | Deposit Date | ATCC No. |
|--------|--------------|----------|
| pTaf02 | | |

This deposit was made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organism will be made available by ATCC under the terms of the Budapest Treaty, and subject to an agreement between Applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

We claim:

1. A purified thermostable enzyme derived from the eubacterium *Thermosipho africanus*, wherein said enzyme has a molecular weight of approximately 103,000 daltons and is characterized as having (a) DNA polymerase activity;

(b) 5'→3' exonuclease activity;

(c) 3'→5' exonuclease activity; and (d) a temperature optimum greater than 45° C.

2. The enzyme of claim 1 consisting essentially of amino acids 1 through 892 of SEQ ID NO: 2.

* * * * *